United States Patent
Kukla et al.

(10) Patent No.: US 7,034,019 B2
(45) Date of Patent: Apr. 25, 2006

(54) PRODRUGS OF HIV REPLICATION INHIBITING PYRIMIDINES

(75) Inventors: Michael Joseph Kukla, Maple Glen, PA (US); Donald William Ludovici, Quakertown, PA (US); Robert William Kavash, Glenside, PA (US); Bart Lieven Daniel De Corte, Southampton, PA (US); Jan Heeres, Vosselaar (BE); Paul Adriaan Jan Janssen, Vosselaar (BE); Lucien Maria Henricus Koymans, Retie (BE); Marc René de Jonge, Tilburg (NL); Koen Jeanne Alfons Van Aken, Kortrijk (BE); Alain Krief, Namur (BE)

(73) Assignee: Janssen Pharmaceutica N.V., Beerse (BE)

( * ) Notice: Subject to any disclaimer, the term of this patent is extended or adjusted under 35 U.S.C. 154(b) by 167 days.

(21) Appl. No.: 10/275,333

(22) PCT Filed: May 3, 2001

(86) PCT No.: PCT/EP01/04990

§ 371 (c)(1),
(2), (4) Date: Nov. 7, 2002

(87) PCT Pub. No.: WO01/85699

PCT Pub. Date: Nov. 15, 2001

(65) Prior Publication Data

US 2003/0186990 A1    Oct. 2, 2003

Related U.S. Application Data

(60) Provisional application No. 60/202,471, filed on May 8, 2000.

(51) Int. Cl.
 *C07D 239/46* (2006.01)
 *C07D 239/48* (2006.01)
 *C07D 401/12* (2006.01)
 *A61K 31/505* (2006.01)

(52) U.S. Cl. .................. 514/235.8; 514/272; 514/275; 544/123; 544/321; 544/326; 544/327; 544/328; 544/329

(58) Field of Classification Search ................ 544/123, 544/321, 326, 327, 328, 329; 514/235.8, 514/272, 275
See application file for complete search history.

(56) References Cited

U.S. PATENT DOCUMENTS

| 2,748,122 A | * | 5/1956 | Burtner ................ 544/332 |
| 5,017,466 A |   | 5/1991 | Kobayashi et al. |
| 6,200,977 B1 |  | 3/2001 | Cushing et al. |
| 6,528,513 B1 |  | 3/2003 | Cushing et al. |
| 6,835,726 B1 |  | 12/2004 | Cushing et al. |

FOREIGN PATENT DOCUMENTS

| EP | 0588762 A | 3/1994 |
| EP | 0834507 A | 4/1996 |
| EP | 0795549 A | 9/1997 |
| EP | 0270111 A | 6/1998 |
| EP | 0945443 A | 9/1999 |
| WO | WO 9118887 A | 12/1991 |
| WO | WO 9510506 A | 4/1995 |
| WO | WO 9719065 A | 5/1997 |
| WO | WO 9641512 A | 9/1998 |
| WO | WO 9931073 A | 6/1999 |
| WO | WO 9950256 A | 10/1999 |
| WO | WO 0039101 A | 7/2000 |

OTHER PUBLICATIONS

Marcus et al., PubMed Abstract (Intervirology 45(4-6):260-6), 2002.*
van Heeswijk et al., PubMed Abstract (Antivir Ther. 6(4): 201-29), Dec. 2001.*
Franke et al., CAPLUS Abstract 106:14707, 1987.*

* cited by examiner

*Primary Examiner*—Deepak Rao
(74) *Attorney, Agent, or Firm*—Laura Donnelly

(57) ABSTRACT

The present invention concerns compounds of formula ($A^1$) ($A_2$)N—$R^1$ (I), the N-oxide forms, the pharmaceutically acceptable addition salts, the quaternary amines and stereochemically isomeric forms thereof, wherein $R^1$ is substituted $C_{1-6}$alkyl; —S(=O)—$R^8$; —S(=O)$_2$—$R^8$; $C_{7-12}$alkylcarbonyl; optionally substituted $C_{1-6}$alkyloxycarbonyl$C_{1-6}$alkylcarbonyl; with $R^8$ being $C_{1-6}$alkyl, aryl$^1$ or Het$^1$; ($A_1$) ($A_2$)N— is the covalently bonded form of the corresponding intermediate of formula ($A_1$)($A_2$)N—H, which is a HIV replication inhibiting pyrimidine of formula (II)

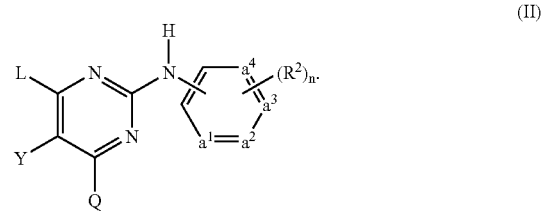

121 Claims, No Drawings

PRODRUGS OF HIV REPLICATION INHIBITING PYRIMIDINES

CROSS REFERENCE TO RELATED APPLICATIONS

This Application is a National Stage Application under 35 U.S.C. § 371 of PCT/EP01/04990, filed May 3, 2001, which claims priority to U.S. Provisional Application Ser. No. 60/202,471, filed May 8, 2000, all of which are incorporated herein by reference in their entirety.

The present invention concerns prodrugs of HIV (Human Immunodeficiency Virus) replication inhibiting pyrimidines. It also relates to their use as a medicine, in particular to their use for the manufacture of a medicament for the treatment of viral infections, to their preparation and compositions comprising them.

WO 99/50250 and WO 00/27825 disclose substituted amino pyrimidine derivatives having HIV inhibiting properties.

EP-B1-0,270,111 describes pyrimidine derivatives having fungicidal activity. WO 95/10506 concerns N-alkyl-N-aryl-pyrimidinamines including acetonitrile, [[2-bromo-4-(1-methylethyl)phenyl](4,6-dimethyl-2-pyrimidinyl)amino]-; acetonitrile, [[2-bromo-4-(1-methylethyl)phenyl](4,6-dimethyl-2-pyrimidinyl)amino]-, monohydrochloride; 1,2-ethanediamine, N-[2-bromo-4-(1-methylethyl)phenyl]-N-(4,6-dimethyl-2-pyrimidinyl)-N',N'-diethyl; and 1,2-ethanediamine, N-[2-bromo-4-(1-methylethyl)phenyl]-N-(4,6-dimethyl-2-pyrimidinyl)-N',N'-dimethyl. Said compounds are disclosed as antagonists at the CRF (Corticotropin Releasing Factor) receptor and are claimed to have a therapeutic effect on psychiatric disorders and neurological diseases.

The present invention concerns substituted amino pyrimidine derivatives which differ in structure and pharmacological profile from the prior art compounds. The present compounds are prodrugs of HIV replication inhibiting compounds. This implies that they are converted after being administered to the subject in need thereof into the corresponding pyrimidine-type HIV replication inhibitors per se.

The present invention concerns a compound of formula $$(A_1)(A_2)N\text{—}R^1 \qquad (I)$$

a N-oxide form, a pharmaceutically acceptable addition salt, a quaternary amine and a stereochemically isomeric form thereof, wherein $R^1$ is $C_{1-6}$alkyl substituted with cyano, amino, mono- or di($C_{1-4}$alkyl)amino, nitro, $C_{1-12}$alkyloxy, hydroxy$C_{1-12}$alkyloxy, $C_{1-6}$alkyloxy$C_{1-12}$alkyloxy, $C_{1-6}$alkylcarbonyloxy$C_{1-12}$alkyloxy, aryl$^1$carbonyloxy$C_{1-12}$alkyloxy or Het$^1$carbonyloxy$C_{1-12}$alkyloxy; —S(=O)—$R^8$; —S(=O)$_2$—$R^8$; $C_{7-12}$alkylcarbonyl; $C_{1-6}$alkyloxycarbonyl$C_{1-6}$alkylcarbonyl; hydroxycarbonyl$C_{1-6}$alkylcarbonyl; aryl$^1$$C_{1-6}$alkyloxycarbonyl$C_{1-6}$alkylcarbonyl; Het$^1$$C_{1-6}$alkyloxycarbonyl$C_{1-6}$alkylcarbonyl; $R^9R^{10}$N—$C_{1-6}$alkyloxycarbonyl$C_{1-6}$alkylcarbonyl;

($A_1$)($A_2$)N— is the covalently bonded form of the corresponding intermediate of formula ($A_1$)($A_2$)N—H, wherein said intermediate of formula ($A_1$)($A_2$)N—H is a pyrimidine of formula

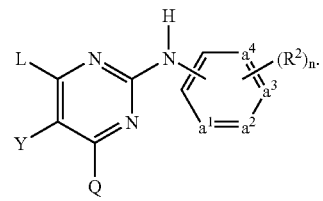

a N-oxide, a pharmaceutically acceptable addition salt, a quatermary amine and a stereochemically isomeric form thereof, wherein -$a^1$=$a^2$-$a^3$=$a^4$- represents a bivalent radical of formula

n is 0, 1, 2, 3 or 4; and in case -$a^1$=$a^2$-$a^3$=$a^4$- is (a-1), then n may also be 5;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, aminocarbonyl, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

wherein each $A_1$ independently is N, CH or CR$^6$; and $A_2$ is NH, O, S or NR$^6$;

L is $C_{1-10}$alkyl, $C_{2-10}$alkenyl, $C_{2-10}$alkyny), $C_{3-7}$cycloalkyl, whereby each of said groups is substituted with one or two substituents independently selected from $C_{3-7}$cycloalky), indolyl or isoindolyl, each optionally substituted with one, two, three or four substituents each independently selected from halo, $C_{1-6}$alkyl, hydroxy, $C_{1-6}$alkyloxy, cyano, aminocarbonyl, nito, amino, polyhalomethyl, polyhalomethyloxy and $C_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined for $R^2$; or L is —X—$R^3$ or —$X^2$-Alk-$R^{11}$ wherein Alk is $C_{1-4}$alkanediyl;

$R^3$ and $R^{11}$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ and $X^2$ each independently are $-NR^7-$, $-NH-NH-$, $-N=N-$, $-O-$, $-C(=O)-$, $-CHOH-$, $-S-$, $-S(=O)-$ or $-S(=O)_2-$;

Q represents hydrogen, $C_{1-6}$alkyl, halo, polyhalo$C_{1-6}$alkyl or $-NR^4R^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, $C_{1-12}$alkylthiocarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, $-S(=O)_pR^{12}$, $-NH-S(=O)_pR^{12}$, $-C(=O)R^{12}$, $-NHC(=O)H$, $-C(=O)NHNH_2$, $-NHC(=O)R^{12}$, $-C(=NH)R^{12}$, aryl and Het; or $R^4$ and $R^5$ taken together may form pyrrolidinyl, piperidinyl, morpholinyl, azido or mono- or di($C_{1-12}$alkyl)amino$C_{1-4}$alkanediyl;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

$R^8$ is $C_{1-6}$alkyl, aryl$^1$ or Het$^1$;

$R^9$ and $R^{10}$ each independently are selected from hydrogen, $C_{1-4}$alkyl, amino$C_{1-4}$alkyl, mono- or di($C_{1-4}$alkyl)amino$C_{1-4}$alkyl; or $R^9$ and $R^{10}$ are taken together to form a bivalent radical of formula $-CH_2-CH_2-Z-CH_2-CH_2-$ with Z being O, $NR^{13}$, $CH_2$, or a direct bond;

$R^{12}$ is methyl, amino, mono- or dimethylamino or polyhalomethyl;

$R^{13}$ is hydrogen, $C_{1-4}$alkyl, amino$C_{1-4}$alkyl, mono- or di($C_{1-4}$alkyl)amino$C_{1-4}$alkyl;

$R^{14}$ is methyl, amino, mono- or dimethylamino or polyhalomethyl;

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or $-C(=O)R^{14}$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^{14}$, $-NH-S(=O)_pR^{14}$, $-C(=O)R^{14}$, $-NHC(=O)H$, $-C(=O)NHNH_2$, $-NHC(=O)R^{14}$, $-C(=NH)R^{14}$ or aryl;

p is 1 or 2;

aryl$^1$ is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, amino, mono- or di($C_{1-4}$alkyl)amino, polyhalo$C_{1-6}$alkyl and polyhalo$C_{1-6}$alkyloxy;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het$^1$ is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl; said partially saturated heterocyclic radical is selected from imidazolinyl, pyrazolinyl, pyrrolinyl, 4,5-dihydro-oxazolyl, 4,5-dihydro-thiazolyl, dihydrofuranyl, dihydrothienyl; and said aromatic heterocyclic radical is selected from pyrrolyl, furanyl, thienyl, imidazolyl, oxazolyl, thiazolyl, pyridyl, pyrimidinyl, pyrazinyl and pyridazinyl wherein each of said aromatic heterocyclic radicals may optionally be substituted with $C_{1-4}$alkyl;

Het is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl wherein each of said saturated heterocyclic radicals may optionally be substituted with an oxo group; said partially saturated heterocyclic radical is selected from imidazolinyl, pyrazolinyl, pyrrolinyl, 4,5-dihydro-oxazolyl, 4,5-dihydro-thiazolyl, dihydrofuranyl, dihydrothienyl; and said aromatic heterocyclic radical is selected from pyrrolyl, furanyl, thienyl, pyridyl, pyrimidinyl, pyrazinyl and pyridazinyl wherein each of said aromatic heterocyclic radicals may optionally be substituted with hydroxy;

provided that acetonitrile, [[2-bromo-4-(1-methylethyl)phenyl](4,6-dimethyl-2-pyrimidinyl)-amino]-;

acetonitrile, [[2-bromo-4-(1-methylethyl)phenyl](4,6-dimethyl-2-pyrimidinyl)amino]-, monohydrochloride;

1,2-ethanediamine, N-[2-bromo-4-(1-methylethyl)phenyl]-N-(4,6-dimethyl-2-pyrimidinyl)-N',N'-diethyl;

1,2-ethanediamine, N-[2-bromo-4-(1-methylethyl)phenyl]-N-(4,6-dimethyl-2-pyrimidinyl)-N',N'-dimethyl are not included.

The present invention also concerns the use of a compound for the manufacture of a medicament for the prevention or the treatment of HIV (Human Immunodeficiency Virus) infection, wherein the compound is a compound of formula $$(A_1)(A_2)N-R^1 \qquad (I)$$

a N-oxide form, a pharmaceutically acceptable addition salt, a quaternary amine and a stereochemically isomeric form thereof, wherein $R^1$ is $C_{1-6}$alkyl substituted with cyano, amino, mono- or di($C_{1-4}$alkyl)amino, nitro, $C_{1-12}$alkyloxy, hydroxy$C_{1-12}$alkyloxy, $C_{1-6}$alkyloxy$C_{1-12}$alkyloxy, $C_{1-6}$alkylcarbonyloxy$C_{1-12}$alkyloxy, aryl$^1$carbonyloxy$C_{1-12}$alkyloxy or Het$^1$carbonyloxy$C_{1-12}$alkyloxy; $-S(=O)-R^8$; $-S(=O)_2-R^8$; $C_{7-12}$alkylcarbonyl; $C_{1-6}$alkyloxycarbonyl$C_{1-6}$alkylcarbonyl; hydroxycarbonyl$C_{1-6}$alkylcarbonyl; aryl$^1C_{1-6}$alkyloxycarbonyl$C_{1-6}$alkylcarbonyl; Het$^1C_{1-6}$alkyloxycarbonyl-$C_{1-6}$alkylcarbonyl; $R^9R^{10}N-C_{1-6}$alkyloxycarbonyl$C_{1-6}$alkylcarbonyl;

$(A_1)(A_2)N-$ is the covalently bonded form of the corresponding intermediate of formula $(A_1)(A_2)N-H$, wherein said intermediate of formula $(A_1)(A_2)N-H$ is a pyrimidine of formula

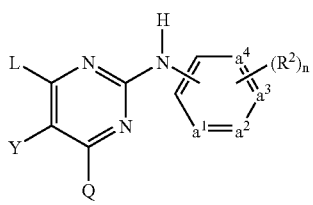

(II)

a N-oxide, a pharmaceutically acceptable addition salt, a quaternary amine and a stereochemically isomeric form thereof, wherein
-$a^1$=$a^2$-$a^3$=$a^4$- represents a bivalent radical of formula —CH=CH—CH=CH— (a-1);

—N=CH—CH=CH— (a-2);

—N=CH—N=CH— (a-3);

—N=CH—CH=N— (a-4);

—N=N—CH=CH— (a-5);

n is 0, 1, 2, 3 or 4; and in case -$a^1$=$a^2$-$a^3$=$a^4$- is (a-1), then n may also be 5;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, aminocarbonyl, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

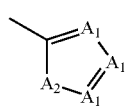

(c)

wherein each $A_1$ independently is N, CH or C$R^6$; and $A_2$ is NH, O, S or N$R^6$;

L is $C_{1-10}$alkyl, $C_{2-10}$alkenyl, $C_{2-10}$alkynyl, $C_{3-7}$cycloalkyl, whereby each of said groups may be substituted with one or two substituents independently selected from
  $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
  phenyl, pyridyl, pyrimidinyl, pyrazinyl or pyridazinyl, wherein each of said aromatic rings may optionally be substituted with one, two, three, four or five substituents each independently selected from the substituents defined for $R^2$; or L is —$X^1$—$R^3$ or —$X^2$-Alk-$R^1$ wherein
  Alk is $C_{1-4}$alkanediyl;
  $R^3$ and $R^{11}$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ and $X^2$ each independently are —N$R^7$—, —NH—NH—, —N=N—, —O—, —C(=O)—, —CHOH—, —S—, —S(=O)— or —S(=O)$_2$—;

Q represents hydrogen, $C_{1-6}$alkyl, halo, polyhalo$C_{1-6}$alkyl or —N$R^4$$R^5$; and $R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, $C_{1-12}$alkylthiocarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$$R^{12}$, —NH—S(=O)$_p$$R^{12}$, —C(=O)$R^{12}$, —NHC(=O)H, —C(=O)NHNH$_2$, —NHC(=O)$R^{12}$, —C(=NH)$R^{12}$, aryl and Het; or $R^4$ and $R^5$ taken together may form pyrrolidinyl, piperidinyl, morpholinyl, azido or mono- or di($C_{1-12}$alkyl)amino$C_{1-4}$alkanediyl;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

$R^8$ is $C_{1-6}$alkyl, aryl$^1$ or Het$^1$;

$R^9$ and $R^{10}$ each independently are selected from hydrogen, $C_{1-4}$alkyl, amino$C_{1-4}$alkyl, mono- or di($C_{1-4}$alkyl)amino$C_{1-4}$alkyl; or $R^9$ and $R^{10}$ are taken together to form a bivalent radical of formula —CH$_2$—CH$_2$-Z-CH$_2$—CH$_2$— with Z being O, N$R^{13}$, CH$_2$, or a direct bond;

$R^{12}$ is methyl, amino, mono- or dimethylamino or polyhalomethyl;

$R^{13}$ is hydrogen, $C_{1-4}$alkyl, amino$C_{1-4}$alkyl, mono- or di($C_{1-4}$alkyl)amino$C_{1-4}$alkyl;

$R^{14}$ is methyl, amino, mono- or dimethylamino or polyhalomethyl;

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^{14}$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^{14}$, —NH—S(=O)$_p$$R^{14}$, —C(=O)$R^{14}$, —NHC(=O)H, —C(=O)NHNH$_2$, —NHC(=O)$R^{14}$, —C(=NH)$R^{14}$ or aryl;

p is 1 or 2;

aryl$^1$ is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, amino, mono- or di($C_{1-4}$alkyl)amino, polyhalo$C_{1-6}$alkyl and polyhalo$C_{1-6}$alkyloxy;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het$^1$ is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl; said partially saturated heterocyclic radical is selected from imidazolinyl, pyrazolinyl, pyrrolinyl, 4,5-dihydro-oxazolyl, 4,5-dihydro-thiazolyl, dihydrofuranyl, dihydrothienyl; and said aromatic heterocyclic radical is selected from pyrrolyl, furanyl, thienyl, imidazolyl, oxazolyl, thiazolyl, pyridyl, pyrimidinyl, pyrazinyl and pyridazinyl wherein each of said aromatic heterocyclic radicals may optionally be substituted with $C_{1-4}$alkyl;

Het$^1$ is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl wherein each of said saturated heterocyclic radicals may optionally be substituted with an oxo group; said partially saturated heterocyclic radical is selected from imidazolinyl, pyrazolinyl, pyrrolinyl, 4,5-dihydro-oxazolyl, 4,5-dihydro-thiazolyl, dihydrofuranyl, dihydrothienyl; and said aromatic heterocyclic radical is selected from pyrrolyl, furanyl, thienyl, pyridyl, pyrimidinyl, pyrazinyl and pyridazinyl wherein each of said aromatic heterocyclic radicals may optionally be substituted with hydroxy.

As used in the foregoing definitions and hereinafter $C_{1-4}$alkyl as a group or part of a group encompasses the straight and branched chain saturated hydrocarbon radicals having from 1 to 4 carbon atoms such as, for example, methyl, ethyl, propyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-10}$alkyl as a group or part of a group defines straight or branched chain saturated hydrocarbon radicals having from 1 to 10 carbon atoms such as the groups defined for $C_{1-6}$alkyl and heptyl, octyl, nonyl, decyl and the like; $C_{1-12}$alkyl as a group or part of a group defines straight or branched chain saturated hydrocarbon radicals having from 1 to 12 carbon atoms such as the groups defined for $C_{1-10}$alkyl and undecyl, dodecyl and the like; $C_{7-12}$alkyl as a group or part of a group encompasses the straight and branched chain saturated hydrocarbon radicals having from 7 to 12 carbon atoms such as, for example, heptyl, octyl, nonyl, decyl, undecyl, dodecyl, 2-methyl-heptyl, 4-ethyl-nonyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-10}$alkenyl defines straight and branched chain hydrocarbon radicals having from 2 to 10 carbon atoms containing a double bond such as the groups defined for $C_{2-6}$alkenyl and heptenyl, octenyl, nonenyl, decenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; $C_{2-10}$alkynyl defines straight and branched chain hydrocarbon radicals having from 2 to 10 carbon atoms containing a triple bond such as the groups defined for $C_{2-6}$alkynyl and heptynyl, octynyl, nonynyl, decynyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoroethyl and the like. In case more than one halogen atoms are attached to an alkyl group within the definition of polyhalomethyl or polyhalo$C_{1-6}$alkyl, they may be the same or different.

Het or Het$^1$ are meant to include all the possible isomeric forms of the heterocycles mentioned in the definitions of Het or Het$^1$, for instance, pyrrolyl also includes 2H-pyrrolyl.

The Het or Het$^1$ radical may be attached to the remainder of the molecule of formula (I) through any ring carbon or heteroatom as appropriate. Thus, for example, when the heterocycle is pyridyl, it may be 2-pyridyl, 3-pyridyl or 4-pyridyl.

When any variable (eg. aryl, $R^2$ etc.) occurs more than one time in any constituent, each definition is independent.

Lines drawn into ring systems from substituents indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethyl amine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The N-oxide forms of the present compounds are meant to comprise the compounds of formula (I) wherein one or several nitrogen atoms are oxidized to the so-called N-oxide.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

An interesting group of compounds are those compounds of formula (I) wherein the $(A_1)(A_2)N—$ moiety is the covalently bonded form of the corresponding intermediate of formula $(A'_1)(A'_2)N—H$, said compounds being represented by formula $(A'_1)(A'_2)N—R^1$ (I') wherein said corresponding intermediate of formula $(A'_1)(A'_2)N—H$ is a pyrimidine of formula

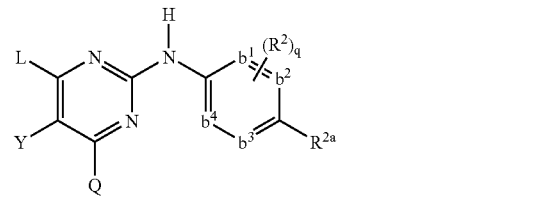

a N-oxide, an addition salt, a quaternary amine and a stereochemically isomeric form thereof, wherein
$-b^1=b^2-C(R^{2a})=b^3-b^4=$ represents a bivalent radical of formula $$—CH=CH—C(R^{2a})=CH—CH= \quad (b-1);$$

$$—N=CH—C(R^{2a})=CH—CH= \quad (b-2);$$

$$—CH=N—C(R^{2a})=CH—CH= \quad (b-3);$$

$$—N=CH—C(R^{2a})=N—CH= \quad (b-4);$$

$$—N=CH—C(R^{2a})=CH—N= \quad (b-5);$$

$$—CH=N—C(R^{2a})=N—CH= \quad (b-6);$$

$$—N=N—C(R^{2a})=CH—CH= \quad (b-7);$$

q is 0, 1, 2; or where possible q is 3 or 4;
$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;
each $R^2$ independently is hydroxy, halo, $C_{1-6}$alkyl optionally substituted with cyano or $—C(=O)R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $—S(=O)_pR^6$, $—NH—S(=O)_pR^6$, $—C(=O)R^6$, $—NHC(=O)H$, $—C(=O)NHNH_2$, $—NHC(=O)R^6$, $—C(=NH)R^6$ or a radical of formula

wherein each $A_1$ independently is N, CH or $CR^6$; and
$A_2$ is NH, O, S or $NR^6$;
p is 1 or 2;
$R^6$ is methyl, amino, mono- or dimethylamino or polyhalomethyl; and L, Y and Q are as defined hereinabove for the intermediates of formula (II).

A special group of compounds contains those compounds of formula (I) or (I') wherein $R^1$ is $C_{1-6}$alkyl substituted with cyano, $C_{1-12}$alkyloxy, hydroxy$C_{1-12}$alkyloxy, $C_{1-6}$alkyloxyC$_{1-12}$alkyloxy or aryl$^1$carbonyloxyC$_{1-12}$alkyloxy; —S(=O)$^2$—R$^8$ with R$^8$ being C$_{1-6}$alkyl, aryl$^1$ or Het$^1$; C$_{7-12}$alkylcarbonyl; R$^9$R$^{10}$N—C$_{1-6}$alkyloxycarbonylC$_{1-6}$alkyl-carbonyl with R$^9$ and R$^{10}$ each independently being selected from C$_{1-4}$alkyl, mono- or di(C$_{1-4}$alkyl)aminoC$_{1-4}$alkyl or R$^9$ and R$^{10}$ are taken together to form a bivalent radical of formula —CH$_2$—CH$_2$—O—CH$_2$—CH$_2$—.

Another special group of compounds contains those compounds of formula (I) or (I') wherein R$^1$ is C$_{1-6}$alkyl substituted with cyano, C$_{1-12}$alkyloxy, hydroxyC$_{1-12}$alkyloxy, C$_{1-6}$alkyloxyC$_{1-12}$alkyloxy or aryl$^1$carbonyloxyC$_{1-12}$alkyloxy.

Another special group of compounds contains those compounds of formula (I) wherein one or more, preferably all, of the following restrictions apply in the covalently bonded form of the pyrimidine compound of formula (II):
i) -a$^1$=a$^2$-a$^3$=a$^4$- is a radical of formula (a-1);
ii) n is 1;
iii) R$^2$ is cyano, preferably in the para position relative to the —NH— group;
iv) Y is hydrogen, cyano, —C(=O)NH$_2$ or a halogen, preferably a halogen;
v) Q is hydrogen or —NR$^4$R$^5$ wherein R$^4$ and R$^5$ are preferably hydrogen;
vi) L is —X—R$^3$; preferably wherein X is NR$^7$, O or S, most preferably wherein X is NH, and preferably wherein R$^3$ is substituted phenyl, most preferably phenyl substituted with one, two or three substituents each independently selected from C$_{1-6}$alkyl, halo and cyano.

Another special group of compounds contains those compounds of formula (I') wherein one or more, preferably all, of the following restrictions apply in the covalently bonded form of the pyrimidine compound of formula (II'):
i) -b$^1$=b$^2$-C(R$^{2a}$)=b$^3$-b$^4$= is a radical of formula (b-1);
ii) q is 0;
iii) R$^{2a}$ is cyano or —C(=O)NH$_2$, preferably R$^{2a}$ is cyano;
iv) Y is hydrogen, cyano, —C(=O)NH$_2$ or a halogen, preferably a halogen;
v) Q is hydrogen or —NR$^4$R$^5$ wherein R$^4$ and R$^5$ are preferably hydrogen;
vii) L is —X—R$^3$; preferably wherein X is NR$^7$, O or S, most preferably wherein X is NH, and preferably wherein R$^3$ is substituted phenyl, most preferably phenyl substituted with one, two or three substituents each independently selected from C$_{1-6}$alkyl, halo and cyano.

An interesting group of compounds are those compounds of formula (I) or (I') wherein L is —X—R$^3$ wherein R$^3$ is 2,4,6-trisubstituted phenyl, each substituent independently selected from chloro, bromo, fluoro, cyano or C$_{1-4}$alkyl.

Also interesting are those compounds of formula (I) or (I') wherein Y is hydrogen, chloro or bromo and Q is hydrogen or amino.

Particular compounds are those compounds of formula (I) wherein in the formula of the corresponding pyrimidine of formula (II) -a$^1$=a$^2$-a$^3$=a$^4$- represents a bivalent radical of formula —CH=CH—CH=CH— (a-1), R$^2$ is 4-cyano and n is 1.

Also particular compounds are those compounds of formula (I') wherein in the formula of the corresponding pyrimidine of formula (II') -b$^1$=b$^2$-C(R$^{2a}$)=b$^3$-b$^4$= represents a bivalent radical of formula —CH=CH—C(R$^{2a}$)=CH—CH= (b-1), R$^{2a}$ is cyano and q is 0.

Preferred compounds are those compounds of formula (I) wherein in the formula of the corresponding pyrimidine of formula (II) -a$^1$=a$^2$-a$^3$=a$^4$- represents a bivalent radical of formula —CH=CH—CH=CH— (a-1), R$^2$ is 4-cyano and n is 1, L is —X—R$^3$ wherein R$^3$ is a 2,4,6-trisubstituted phenyl, Y is hydrogen or halo and Q is hydrogen or NH$_2$.

Also preferred compounds are those compounds of formula (I') wherein in the formula of the corresponding pyrimidine of formula (II') -b$^1$=b$^2$-C(R$^{2a}$)=b$^3$-b$^4$= represents a bivalent radical of formula —CH=CH—C(R$^{2a}$)=CH—CH= (b-1), R$^{2a}$ is cyano and q is 0, L is —X—R$^3$ wherein R$^3$ is a 2,4,6-trisubstituted phenyl, Y is hydrogen or halo and Q is hydrogen or NH$_2$.

Most preferred compounds of formula (I) or (I') are those compounds wherein the corresponding pyrimidine compound of formula (II) or (II') is:
4-[[4-amino-5-chloro-6-[(2,4,6-trimethylphenyl)amino]-2-pyrimidinyl]amino]-benzonitrile;
4-[[5-chloro-4-[(2,4,6-trimethylphenyl)amino]-2-pyrimidinyl]amino]benzonitrile;
4-[[5-bromo-4-(4-cyano-2,6-dimethylphenoxy)-2-pyrimidinyl]amino]benzonitrile;
4-[[4-amino-5-chloro-6-[(4-cyano-2,6-dimethylphenyl)amino]-2-pyrimidinyl]amino]-benzonitrile;
4-[[5-bromo-6-[(4-cyano-2,6-dimethylphenyl)amino]-2-pyrimidinyl]amino]benzonitrile;
4-[[4-amino-5-chloro-6-(4-cyano-2,6-dimethylphenyloxy)-2-pyrimidinyl]amino]-benzonitrile;
4-[[4-amino-5-bromo-6-(4-cyano-2,6-dimethylphenyloxy)-2-pyrimidinyl]amino]-benzonitrile;
4-[[4-[(2,4,6-trimethylphenyl)amino]-2-pyrimidinyl]amino] benzonitrile; and
4-[[2-[(4-cyanophenyl)amino]-4-pyrimidinyl]amino]-3,5-dimethylbenzonitrile; the N-oxides, the addition salts, the quaternary amines and the stereochemically isomeric forms thereof.

In general, compounds of formula (I) can be prepared by reacting an HIV replication inhibiting intermediate of formula (A$_1$)(A$_2$)N—H with an intermediate of formula (III), wherein W$_1$ represents a suitable leaving group, such as a halogen, e.g. chloro, bromo and the like, in the presence of a suitable base, such as for example sodium hydride, butyl lithium, sodium hydroxide or N-(1-methylethyl)-2-propanamine, and a suitable reaction-inert solvent, such as for example tetrahydrofuran.

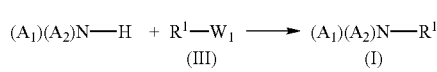

In this and the following preparations, the reaction products may be isolated from the reaction medium and, if necessary, further purified according to methodologies generally known in the art such as, for example, extraction, crystallization, distillation, trituration and chromatography.

Compounds of formula (I), wherein R$^1$ is C$_{1-6}$alkyloxycarbonylC$_{1-6}$alkylcarbonyl, aryl$^1$C$_{1-6}$alkyloxycarbonylC$_{1-6}$alkylcarbonyl, Het$^1$C$_{1-6}$alkyloxycarbonylC$_{1-6}$alkylcarbonyl or R$^9$R$^{10}$N—C$_{1-6}$alkyloxycarbonylC$_{1-6}$alkylcarbonyl, said R$^1$ being represented by R$^{1a}$—O—C(=O)—C$_{1-6}$alkyl-C(=O), and said compounds by formula (I-a), can be prepared by reacting an HIV replication inhibiting intermediate of formula (A$_1$)(A$_2$)N—H with an intermediate of formula (IV), wherein W$_2$ represents a suitable leaving group, such as a halogen, e.g. chloro, bromo and the like, and an intermediate of formula (V) in the presence of a suitable base, such as sodium hydride, and a suitable reaction-inert solvent, such as N,N-dimethylformamide.

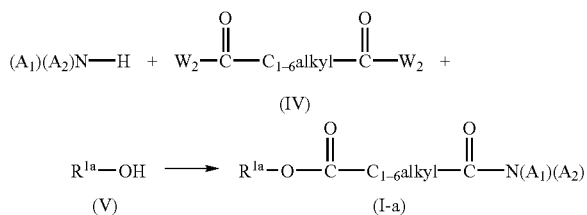

The compounds of formula (I) may further be prepared by converting compounds of formula (I) into each other according to art-known group transformation reactions.

Compounds of formula (I), wherein $R^1$ is hydroxy$C_{1-12}$alkyloxy$C_{1-6}$alkyl, said compounds being represented by formula (I-b), can be prepared by hydrolyzing a compound of formula (I), wherein $R^1$ is $C_{1-6}$alkyl substituted with $C_{1-6}$alkylcarbonyloxy$C_{1-12}$alkyloxy, aryl$^1$carbonyloxy$C_{1-12}$alkyloxy or Het$^1$carbonyloxy$C_{1-12}$alkyloxy, said $R^1$ being represented by $R^{1b}$—C(=O)—O—$C_{1-12}$alkyloxy$C_{1-6}$alkyl, and said compounds being represented by formula (I-c), in the presence of a suitable hydrolysing agent, such as a suitable alkali metal hydroxide or an earth alkaline metal, such as lithium hydroxide, and a suitable reaction-inert solvent, such as tetrahydrofuran and water.

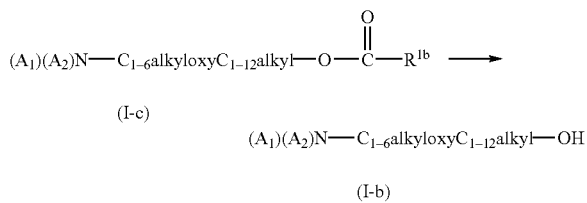

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxide acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures-of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or may be prepared according to the procedures described in WO 99/50250 and WO 00/27825.

In general, the HIV replication inhibiting pyrimidine derivatives of formula (II) can be prepared by reacting an intermediate of formula (VI) wherein $W_3$ is a suitable leaving group such as, for example, a halogen, hydroxy, triflate, tosylate, thiomethyl, methylsulfonyl, trifluoromethylsulfonyl and the like, with an amino derivative of formula (VII) optionally under solvent-free conditions or in a reaction-inert solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether or the like. This reaction can be performed at a temperature ranging between 50° C. and 250° C.

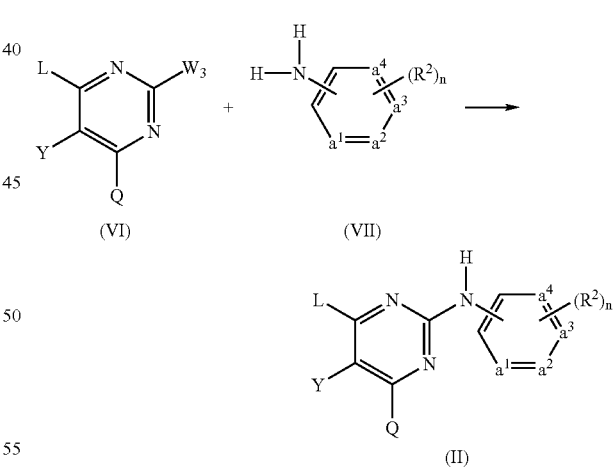

The HIV replication inhibiting pyrimidine intermediates of formula (II), wherein L is a radical of formula —NR$^7$R$^3$, said intermediates being represented by formula (II-a), can be prepared by reacting an intermediate of formula (VIII) wherein $W_4$ is a suitable leaving group such as, for example, a halogen or a triflate, with an intermediate of formula (IX) under solvent-free conditions or in an appropriate solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether. This reaction can be performed at a temperature ranging between 50° C. and 250° C.

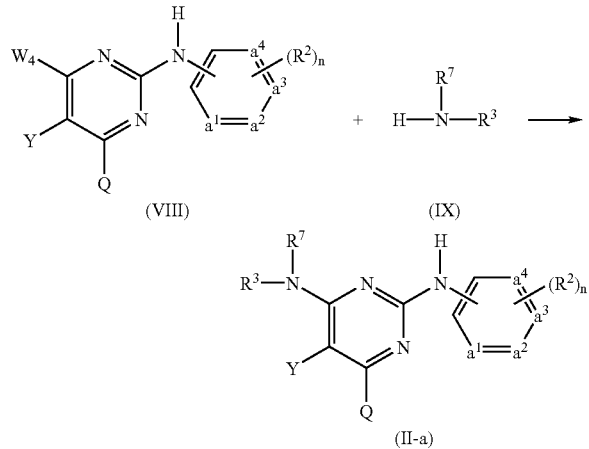

The HIV replication inhibiting pyrimidine intermediates of formula (II), wherein L is a radical of formula —O—$R^3$, said intermediates being represented by formula (II-b), can be prepared by reacting an intermediate of formula (VIII) wherein $W_4$ is a suitable leaving group such as, for example a halogen or a triflate, with an intermediate of formula (X) in an appropriate solvent such as, for example, 1,4-dioxane, dimethyl sulfoxide, tetraline, sulfolane and the like under a reaction-inert atmosphere such as, for example, oxygen free argon or nitrogen, and in the presence of a base such as, for example, sodium hydride, potassium hydride, sodium hydroxide or the like. This reaction can be performed at a temperature ranging between 50° C. and 250° C.

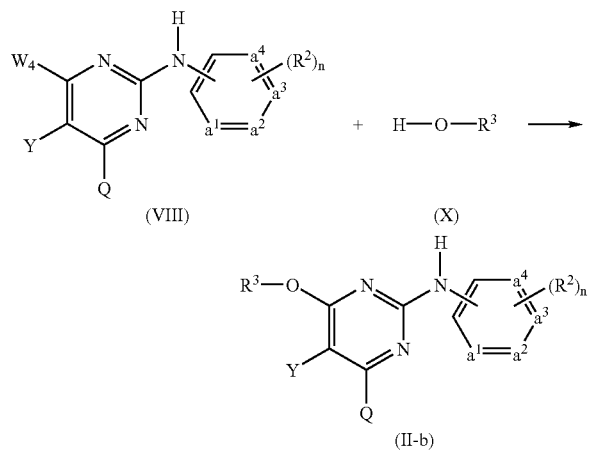

The HIV replication inhibiting pyrimidine intermediates of formula (II) may further be prepared by converting intermediates of formula (II) into each other according to art-known group transformation reactions.

The HIV replication inhibiting pyrimidine intermediates of formula (II) may be converted to the corresponding N-oxide forms following art-known procedures as described hereinabove for the preparation of the N-oxide forms of the compounds of formula (I).

For instance, the HIV replication inhibiting pyrimidine intermediates of formula (I) wherein Q is a halogen may be converted to the corresponding intermediates wherein Q is —$NR^4H$ using $NH_2R^4$ as a reagent in a reaction inert solvent such as, for example, 1,4-dioxane and the like, optionally in the presence of a suitable base such as, for example, N,N-diethylethanamine or N,N-diisopropylethylamine or the like. In case $R^4$ contains a hydroxy moiety, it may be convenient to perform the above reaction with a protected form of $NH_2R^4$ whereby the hydroxy moiety bears a suitable protecting group P being, for instance, a trialkylsilyl group, and subsequently removing the protective group according to art-known methodologies.

Intermediates of formula (VI) wherein L is —X—$R^3$, said intermediates being represented by formula (VI-1) can be prepared by reacting a pyrimidine derivative of formula (XI) wherein each $W_3$ is as defined previously, with $HXR^3$ (XII) in a reaction-inert solvent such as, for example, 1,4-dioxane, 2-propanol or the like, and in the presence of a base such as, for example, N,N-diethylethanamine or N,N-diisopropylethylamine or the like. Different regio-specific isomers may be formed and can be separated from one another using suitable separation techniques such as, for example, chromatography.

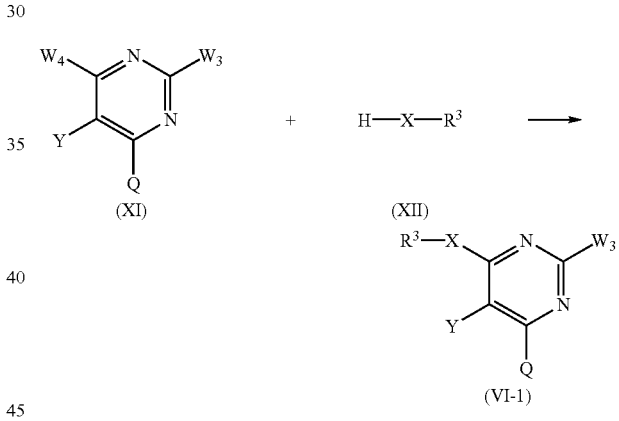

Intermediates of formula (VIII) can be prepared by reacting an intermediate of formula (XI-a) wherein $W_4$ is a suitable leaving group such as, for example, a halogen, with an intermediate of formula (XIII) in a suitable solvent such as, for example, 1-methyl-2-pyrrolidinone, 1,4-dioxane or the like, in the presence of an acid such as, for example, 1 N hydrochloric acid in diethyl ether. This reaction can be performed at a temperature ranging between 50° C. and 250° C.

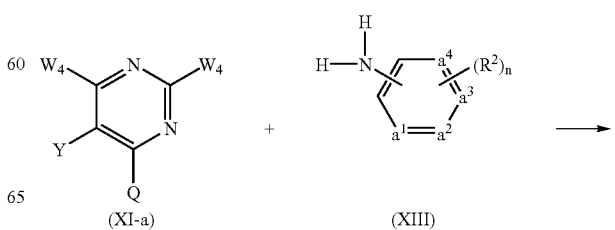

-continued

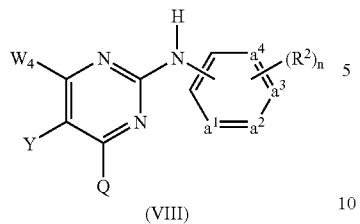

(VIII)

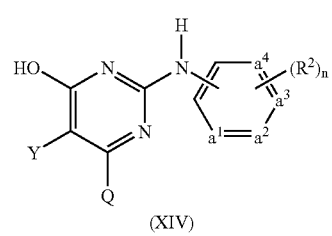

(XIV)

Alternatively, intermediates of formula (VIII) can be prepared by reacting an intermediate of formula (XIV) with a leaving group introducing agent, wherein $W_4$ represents the leaving group and R represents the remaining of the leaving group introducing agent, examples of suitable leaving group introducing agents are phosphorous oxychloride, triflic anhydride or a functional derivative thereof under a reaction-inert atmosphere such as, for example, oxygen free argon or nitrogen. This reaction can be performed at a temperature ranging between 20° C. and 150° C.

Intermediates of formula (XIV) can also be prepared by reacting an intermediate of formula (XVI), wherein $W_5$ is a suitable leaving group such as for example $C_{1-6}$alkyloxy and Y and Q are as defined for an intermediate of formula (II), with an intermediate of formula (XVII) in an appropriate solvent such as, for example, ethanol, or the like, and in the presence of a base such as, for example, sodium ethoxide or the like, under a reaction-inert atmosphere such as, for example, oxygen free argon or nitrogen. The reaction can be performed at a temperature ranging between 20° C. and 125° C.

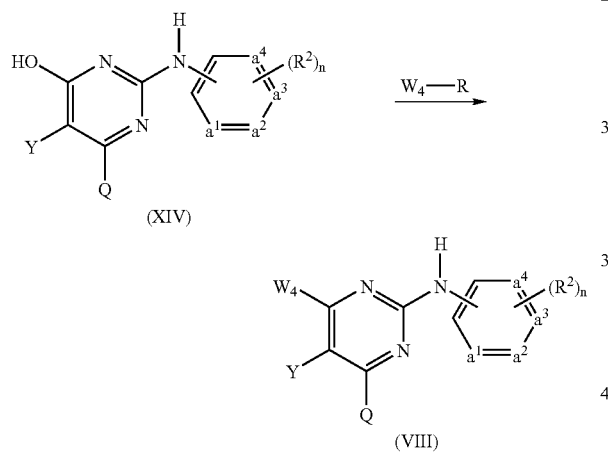

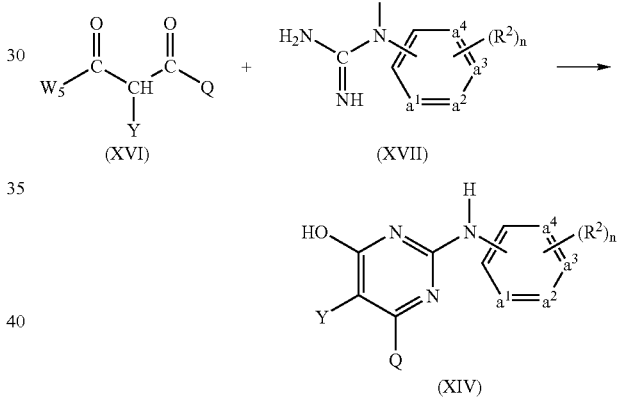

Intermediates of formula (XIV) can be prepared by reacting an intermediate of formula (XV) or a functional derivative thereof, with an intermediate of formula (XIII). This reaction may be performed under solvent-free conditions or in an appropriate solvent such as, for example, diglyme, tetraline or the like under a reaction-inert atmosphere such as, for example, oxygen free argon or nitrogen, and optionally in the presence of a base such as, for example, sodium hydride, potassium hydride or the like. This reaction can be performed at a temperature ranging between 100° C. and 250° C.

A convenient way of preparing an intermediate of formula (VIII) wherein Y is a bromine or chloro atom, said intermediates being represented by formula (VIII-1), involves the introduction of a bromine or chloro atom to an intermediate of formula (XVIII), wherein $W_4$ is as previously defined, using N-bromosuccinimide or N-chlorosuccininide in a reaction-inert solvent such as, for example, chloroform, carbon tetrachloride or the like. This reaction can be performed at a temperature ranging between 20° C. and 125° C.

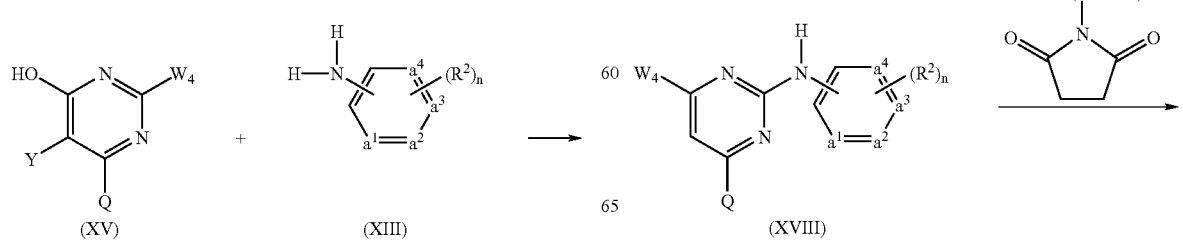

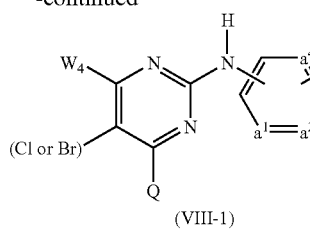

(VIII-1)

Analogous to the conversion of intermediates of formula (II) wherein Q is a halogen to intermediates of formula (II) wherein Q is —NHR$^4$, the intermediates of formula (VI), (VIII) and (XI) can also be converted.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

As described hereinabove, the compounds of the present invention are prodrugs. Prodrugs are pharmacologically acceptable derivatives of drugs per se. After administration to the subject in need thereof, the prodrugs undergo a conversion to the physiologically active species. This conversion may involve an enzymatic or chemical cleavage of a functionality on the prodrug, thus resulting in the release of the corresponding active compound. The reference by Goodman and Gilman (The Pharmacological Basis of Therapeutics, $8^{th}$ ed., McGraw-Hill, Int. Ed. 1992, "Biotransformation of Drugs", p. 13–15) describing prodrugs generally, is hereby incorporated.

The present compounds hydrolyse under physiological conditions releasing the corresponding HIV replication inhibiting (reverse transcriptase inhibitors) pyrimidine derivatives of formula (II) or (II'). The advantage of prodrugs is that they may provide an increased bioavailability than that which could be obtained if the active compound per se was administered; a delayed bioavailability; an enhanced distribution into targeted tissues or an increased biological penetration into a given biological system (e.g. blood, lymphatic system, central nervous system); an altered metabolism and rate of excretion; an increased solubility. An increased solubility may allow administration by injection or by solution, the latter especially being preferred when the patients are children, elderly people or persons with difficulties to swallow. An increased solubility may enhance the bioavailability, and may also contribute to an improvement of the drug load per unit dosage form, which may reduce the patient's pill burden and hence improve the patient compliance. It may also provide for the possibility to increase the daily administered amount of drug.

Due to their conversion under physiological conditions into the HIV replication inhibiting pyrimidines of formula (II) or (II'), the present compounds show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy PGL) and AIDS—related complex (ARC).

The present compounds also show activity against multi drug resistant HIV strains, in particular multi drug resistant HIV-1 strains, more in particular the present compounds show activity against HIV strains, especially HIV-1 strains, that have acquired resistance to art-known non-nucleoside reverse transcriptase inhibitors. Art-known non-nucleoside reverse transcriptase inhibitors are those non-nucleoside reverse transcriptase inhibitors other than the active species of the prodrugs of the present invention. They also have little or no binding affinity to human α-1 acid glycoprotein.

Due to their conversion into compounds having antiretroviral properties, particularly anti-HIV properties, especially anti-HIV-1-activity, the compounds of formula (I) or (I'), their N-oxides, pharmaceutically acceptable addition salts, quaternary amines and stereochemically isomeric forms thereof, are useful in the treatment or prevention of viral infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The present compounds of formula (I) or (I') or any subgroup thereof may therefore be used as medicines, especially against above-mentioned conditions. They may be used in the manufacture of a medicament for the treatment or the prevention of the above-mentioned conditions. Said use as a medicine or method of treatment comprises the systemic administration to HIV-infected subjects of an amount effective to combat the conditions associated with HIV and other pathogenic retroviruses, especially HIV-1.

In view of the utility of the compounds of formula (I) or (I'), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I) or (I'), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) or (I') and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucoses solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the present compounds are prodrugs, which have to be converted into the active compounds per se, it will be appreciated that their dose to be administered will be such as to release an effective therapeutic or prophylactic amount of the active compound per se upon conversion. As used hereinbefore or hereinafter, a therapeutically effective amount of a compound of formula (I) or (I') will define such an amount of a compound of formula (I) or (I') which enables the release of a therapeutically effective amount of the corresponding active compound per se upon conversion. In general it is contemplated that an effective daily amount of the corresponding HIV replication inhibiting pyrimidine derivative per se would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) or (I') used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present prodrugs can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The prodrugs may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

The combination of an antiretroviral compound and a compound of formula (I) or (I') can be used as a medicine. Thus, the present invention also relates to a product containing (a) a compound of formula (I) or (I'), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamnivudine (2'-3'-dideoxy-3'-thiacytidine, 3TC), stavudine (2',3'-didehydro-3'-deoxythymidine, d4T), abacavir and the like; non-nucleoside reverse transciptase inhibitors such as nevirapine (11-cyclopropyl-5,11-di-hydro-4-methyl-6H-dipyrido[3,2-b: 2',3'-e][1,4]diazepin-6-one), efavirenz, delavirdine, TMC-120, TMC-125 and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249, AMD-3100 and the like; inhibitors of the viral integrase; nucleotide reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional antiretroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The prodrugs of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; or cholinergic agents, e.g. tacrine, rivastigmine, donepezil, galantamine and the like to prevent or combat infection and diseases or symptoms of diseases associated with HIV infections, such as AIDS and ARC, e.g. dementia. A compound of formula (I) or (I') can also be combined with another compound of formula (I) or (I').

Although the present invention focuses on the use of the present compounds for preventing or treating HIV infections, the present compounds may also be used as inhibitory agents for other viruses which depend on similar reverse transcriptases for obligatory events in their life cycle.

Experimental Part

In the below described preparations of intermediate compounds and final compounds, HPLC stands for high performance liquid chromatography.

A. Preparation of the Intermediate Compounds

EXAMPLE A1

Reaction under argon atmosphere. A solution of 2,4,6-trimethylbenzenamine (0.00461 mol) in 1,4-dioxane (5 ml) was added to a solution of 5-bromo-2,4-dichloro-pyrimidine (0.00439 mol) in 1,4-dioxane (5 ml). N,N-bis(1-methylethyl)ethanamine (0.00548 mol) was added. The reaction mixture was stirred and refluxed for 20 hours. The solvent was evaporated. The residue was dissolved in ethyl acetate, washed with a saturated aqueous sodium bicarbonate solution, water and brine, dried with sodium sulfate, filtered, and the solvent was evaporated. The residue was purified by column chromatography over silica gel (eluent: 1:5, 1:2 and 1:1 $CH_2Cl_2$: hexane). Two pure fraction groups were collected and their solvent was evaporated, yielding 0.35 g (24%) of 5-bromo-4-chloro-N-(2,4,6-trimethylphenyl)-2-pyrimidinamine (interm. 1) and 0.93 g (65%) of 5-bromo-2-chloro-N-(2,4,6-trimethylphenyl)-4-pyrimidinamine (interm. 2).

EXAMPLE A2 a) 4-Hydroxy-5-chloro-2-methylthiopyrimidine (0.0156 mol) and 4-aminobenzonitrile (0.078-mol) were combined as a melt and stirred at 180–200° C. for 6 hours. The reaction mixture was cooled, and triturated sequentially with boiling $CH_2Cl_2$ and $CH_3CN$ to obtain 95% pure compound, which was dried, yielding 1.27 g (33%) of 4-[(5-chloro-4-hydroxy-2-pyrimidinyl)amino]benzonitrile (interm. 3; mp. >300° C.).

b) $POCl_3$ (10 ml) was added to intermediate (3) (0.0028 mol). The flask was equipped with a condenser and heated to 80° C. for 35 minutes. The material was quenched on ice and the resulting precipitate was collected and washed with water (50 ml). The sample was dried. A fraction thereof was further purified by column chromatography. The pure fractions were collected and the solvent was evaporated, yielding 4-[(4,5-dichloro-2-pyrimidinyl)amino]benzonitrile (interm. 4).

c) The mixture of intermediate (4) (0.0132 mol) in tetrahydrofuran (75 ml) and $CH_2Cl_2$ (10 ml) was stirred for 15 minutes. HCl in diethyl ether (0.0145 mol) was added slowly, and the mixture was stirred for 5 minutes. The solvent was removed under reduced pressure, yielding 3.98 g of 4-[(4,5dichloro-2-pyrimidinyl)amino]benzonitrile monohydrochloride (interm. 5).

EXAMPLE A3 a) 2,4,5,6-tetrachloropyrimidine (0.0134 mol), 1,4-dioxane (30 ml), 2,4,6-trimethyl aniline (0.0134 mol), and N,N-bis(1-methylethyl)ethanamine (0.0136 mol) were added to a flask under argon and stirred at 55° C. for 16 hours. The solvent was evaporated, and the residue was dissolved in $CH_2Cl_2$, then purified by column chromatography over silica gel (eluent: $CH_2Cl_2$/hexane 1/4, and 1/2). The desired fractions were collected and their solvent was evaporated, yielding 0.15 g 4,5,6-trichloro-N-(2,4,6-trimethylphenyl)-2-pyrimidinamine (interm. 6) and 3.15 g 2,5,6-trichloro-N-(2,4,6-trimethylphenyl)4-pyrimidinamine (interm. 7).

b) A mixture of intermediate 7 (0.00474 mol) in $NH_3$, (2.0 M in 2-propanol; 20 ml) was heated in a pressure vessel at 75–80° C. for 40 hours. The temperature was increased to 110–115° C. The solvent was evaporated to produce 1.85 g of residue. The sample was heated with $NH_3$ (0.5 M in 1,4-dioxane; 20 ml) at 125° C. for 18 hours. The solvent was evaporated, yielding 1.7 g of a mixture of two isomers, i.e. 2,5-dichloro-N4-(2,4,6-trimethylphenyl)4,6-pyrimidinediamine (interm. 8) and 5,6-dichloro-N4-(2,4,6-trimethylphenyl)-2,4-pyrimidinediamine (interm. 9).

EXAMPLE A4 a) A mixture of 4-[(1,4-dihydro4-oxo-2-pyrimidinyl) amino]benzonitrile, (0.12 mol) in $POCl_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1000 ml $CH_2Cl_2$ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of 4[(4-chloro-2-pyrimidinyl)amino]benzonitrile (interm. 10).

b) Intermediate (10)(0.005 mol), 1-bromo-2,5-pyrrolidinedione (0.006 mol) and trichloromethane (10 ml) were combined in a sealed tube and heated at 100° C. overnight. The reaction mixture was allowed to cool to room temperature. Silica gel (2 g) was added, and the solvent was evaporated. The residue was purified by flash column chromatography over silica gel (eluent: $CH_2Cl_2$/hexane 9/1). The pure fractions were collected and the solvent was evaporated, yielding 1.31 g (84.5%) of 4-[(5-bromo-4-chloro-2-pyrimidinyl)amino]benzonitrile (interm. 11).

EXAMPLE A5

To a flask under argon was added 4-amino-2,5,6-trichloropyrimidine (0.08564 mol), 4-amino-benzonitrile (0.1071 mol), 1-methyl-2-pyrrolidinone (17 ml) and HCl in diethylether (1M; 85.6 ml). The mixture was placed in an oil bath at 130° C. under a stream of nitrogen until the ether was gone. An additional 10 ml of 1-methyl-2-pyrrolidinone was added. The mixture was heated at 145° C. for 16 hours under argon. 1,4-Dioxane was added. The mixture was refluxed, cooled, then filtered. The filtrate was evaporated. The residue was dissolved in $CH_2Cl_2$, washed with 1 N NaOH, then filtered. The solid was dissolved in 2-propanone, evaporated onto silica gel, and chromatographed using 1–3% 2-propanone in hexane as eluent. The pure fractions were collected and the solvent was evaporated, yielding 1.63 g (6.8%) of 4-[(4-amino-5,6-dichloro-2-pyrimidinyl)amino] benzonitrile (interm. 12).

EXAMPLE A6 a) To a flask under argon containing intermediate (1) (0.00107 mol) was added ether. To this homogeneous solution was added HCl/diethylether (1M; 0.00109 mol). The solvent was evaporated and 1,4-dioxane (35 ml) and 4-aminobenzonitrile (0.00322 mol) were added. The reaction mixture was stirred and refluxed for 4 days. The solvent was evaporated. The residue was dissolved in $CH_2Cl_2$, washed with a saturated sodium bicarbonate solution, dried, filtered and the solvent was evaporated to give 0.79 g of amber oil. The oil was purified by reverse phase HPLC. The desired fractions were collected and the solvent was evaporated, yielding residues 1 and 2. Residue 1 was purified by column chromatography over silica gel (eluent: 0 and 2% $CH_3OH$: $CH_2Cl_2$). The pure fractions were collected and the solvent was evaporated, yielding 0.0079 g (2.0%) of 4-[[5-chloro-2-[(2,4,6-trimethylphenyl)amino]-4-pyrimidinyl]amino] benzonitrile (interm. 13).

Residue 2 was purified by column chromatography over silica gel (eluent: 0 and 2% $CH_3OH$:$CH_2Cl_2$). The pure fractions were collected and the solvent was evaporated, yielding 0.0044 g (1.0%) of 4-[[5-bromo-2-[(2,4,6-trimethylphenyl)amino]-4-pyrimidinyl]amino]benzonitrile (interm. 14).

b) To a flask containing intermediate 2 (0.00285 mol) was added ether. To this homogeneous solution was added HCl in diethyl ether (1M; 0.00855 mol). The solvent was evaporated and 1,4-dioxane (20 ml) was added. Finally, 4-aminobenzonitrile (0.00291 mol) and 1,4-dioxane (15 ml) were added and the reaction mixture was stirred and refluxed for seven days. The solvent was evaporated, the residue dissolved in $CH_2Cl_2$, washed with 1 M NaOH, and the solvent evaporated. The residue was dissolved in $CH_2Cl_2$ (10 ml) and the precipitate was filtered off and dried, yielding 0.15 g (13%) of 4-[[5bromo-4-[(2,4,6-trimethylphenyl)amino]-2-pyrimidinyl]amino]benzonitrile (interm. 15). 4-[[4-[(2,4,6-trimethylphenyl)amino]-2-pyrimidinyl]amino]benzonitrile (interm. 16) was prepared according to an analogous procedure.

EXAMPLE A7 a) A 3:1 mixture of intermediate (8) and intermediate (9) [as prepared in example A3b] and 4-aminobenzonitrile (0.01422 mol) was heated in a pressure vessel at 180° C. for 5 hours. The sample was partitioned between $CH_2Cl_2$ and diluted $NaHCO_3$, dried over $K_2CO_3$, filtered, and evaporated. $CH_3CN$ was stirred in, the resulting precipitate removed by filtration. The filtrate was further purified by reverse phase HPLC. The pure fractions were collected and the solvent was evaporated, yielding 0.17 g of 4-[[4-amino-5-chloro-6-[(2,4,6-trimethylphenyl)amino]-2-pyrimidinyl] amino]benzonitrile trifluoroacetate (1:1) (interm. 17).

EXAMPLE A8

HCl in diethylether (1M; 0.0045 mol) was added to a suspension of intermediate (4) (0.003 mol) in 1,4-dioxane (5 ml), stirred under argon in a sealable tube. The mixture was warmed to evaporate the diethylether, and 2,4,6-trimethylbenzenamine (0.009 mol) was added. The tube was sealed, and the reaction mixture was heated to 150° C. for 12 hours. The reaction mixture was allowed to cool to room temperature. Sequentially, silica gel (2.2 g) and $CH_3OH$ (50 ml) were added. After evaporating the solvent, the residue was purified by flash chromatography (eluent gradient: $CH_2Cl_2$:$CH_3OH$:$NH_4OH$ 99.5:0.45:0.05 up to 99:0.9:0.1). The pure fractions were collected and the solvent was evaporated. The residue was dried, yielding 0.80 g (73.4%) of 4-[[5-chloro-4-[(2,4,6-trimethylphenyl)amino]-2-pyrimidinyl]amino]benzonitrile (interm. 18). 4-[[2-[(4-cyanophenyl)amino]-4-pyrimidinyl]amino]-3,5-dimethylbenzonitrile (interm. 19) was prepared according to an analogous procedure.

EXAMPLE A9

A mixture of intermediate (5) (0.0025 mol) and 2,6-dibromo-4-methylbenzenamine (0.0075 mol) in 1,3-dioxane (5.0 ml) in a sealed tube under argon was heated and stirred at 160° C. for 16 hours. The reaction mixture was concentrated by rotary evaporation onto silica gel (2.0 g). The material was purified by flash chromatography (eluent 1:1 hexane: $CH_2Cl_2$; neat $CH_2Cl_2$; 0.5%, 1% (10% $NH_4OH$ in $CH_3OH$) in $CH_2Cl_2$) for 90% purity. Recrystallization yielded 0.15 g (12.2%) of 4-[[5-chloro-4-[(2,6-dibromo-4-methylphenyl)amino]-2-pyrimidinyl]amino]benzonitrile (interm. 20; 95% purity).

EXAMPLE A10

NaH (0.0075 mol; 60% suspension in oil) was added to a suspension of 2,4,6-trimethylphenol (0.0075 mol) in 1,4-dioxane (5 ml) in a sealable tube under argon. The mixture was stirred for 15 minutes, and intermediate (4) (0.0025 mol) was added. The tube was sealed, and the reaction mixture was heated to 150° C. for 15 hours. The reaction was allowed to cool to room temperature. After silica gel (2.0 g) was added, the solvent was evaporated. The residue was purified by flash column chromatography over silica gel (eluent gradient: $CH_2Cl_2$: hexane 9:1 up to 100:0; then $CH_2Cl_2$:$CH_3OH$:$NH_4OH$ 100:0:0 up to 97:2.7:0.3). The pure fractions were collected and the solvent was evaporated. The residue was dried, yielding 0.73 g of (80.2%) 4-[[5-chloro-4-(2,4,6-trimethylphenoxy)-2-pyrimidinyl]amino]benzonitrile (interm. 21).

EXAMPLE A11

NaH, 60% suspension in oil (0.003 mol) and 1-methyl-2-pyrrolidinone (3 ml) were added to a suspension of 4-hydroxy-3,5-dimethylbenzonitrile (0.003 mol) in 1,4-dioxane (3 ml) in a sealable tube under argon. After the $H_2$ had evolved, intermediate (11) (0.001 mol) was added. The tube was sealed and the reaction mixture was heated to 160° C. for 16 hours. The mixture was cooled to room temperature, transferred to a beaker and diluted with methanol (20 ml). Water (200 ml) was added dropwise. The aqueous mixture was extracted with $CH_2Cl_2$/$CH_3OH$ 90/10 (3×300 ml). The organic layer was separated, dried, filtered and adsorbed onto silica gel (1 g). The solvent was evaporated and the residue was purified by flash column chromatography over silica gel (eluent: $CH_2Cl_2$/$CH_3OH$/$NH_4OH$ from 100/0/0 to 98/1.8/0.2). The desired fractions were collected and the solvent was evaporated. The residue was triturated with hot $CH_3CN$, filtered off, then dried, yielding 0.20 g (47.6%) of 4-[[5-bromo-4-(4-cyano-2,6-dimethylphenoxy)-2-pyrimidinyl]amino]benzonitrile (interm. 22).

EXAMPLE A12

To a pressure vessel under argon was added intermediate 12 (0.00286 mol), 4-cyano-2,6-dimethylaniline (0.00571 mol), 1M HCl in diethyl ether (0.00140 mol) and 1,4-dioxane (8 ml). The reaction mixture was heated in an oil bath under a stream of nitrogen until all the solvents had evaporated. 1-methyl-2-pyrrolidinone (3 ml) was added, and the reaction mixture was heated at 220–240° C. for 3 hours. Heating was continued at 210–220° C. for 6 hours. The residue was dissolved in 1,4-dioxane, evaporated, partitioned between $CH_2Cl_2$ and 1 N NaOH, filtered, organic layers were dried with potassium carbonate and evaporated. The desired compound was isolated and purified by preparative reverse phase chromatography. The pure fractions were collected and the solvent was evaporated, yielding 0.0165 g (1.1% after lyophilization) of 4-[[4-amino-5-chloro-6-[(4-cyano-2,6-dimethylphenyl)amino]-2-pyrimidinyl]amino]benzonitrile trifluoroacetate (1:1) (interm. 23).

EXAMPLE A13

A mixture of intermediate (11) (0.0011 mol), 2,6-dimethyl-4-(2-propyl)benzenamine (0.0011 mol), N,N,N',N'tetramethyl-1,8-naphthalenediamine (0.0022 mol) and 1 M HCl in ether (2.3 ml) (0.0023 mol) in 1,4-dioxane (25 ml) was stirred and heated to 95° C. for 16 hours. Solvent was removed by rotary evaporation and the residue was purified by reverse phase preparatory HPLC. The combined fractions containing the desired material were lyophilized to yield 0.23 g of

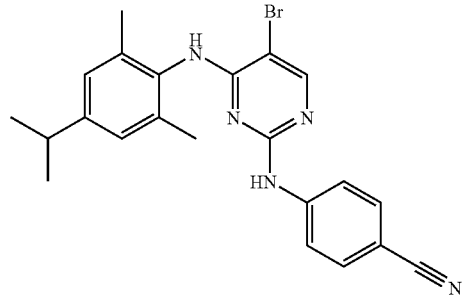

(48%); mp. 198–201° C. (interm. 24)

EXAMPLE A14

N,N-di(methylethyl)ethanamine (0.0024 mol) was added to 4-amino-2,6-dimethyl-3,4-benzonitrile (0.00219 mol) and 4-[[(5-bromo-4,6-dichloro)-2-pyrimidinyl]amino]-benzonitrile (0.00218 mol). The reaction vial was sealed and heated to 155–160° C. with stirring for 1.5 days. The sample was cooled to room temperature. The sample was treated with flash column chromatography over silica gel (eluent: $CH_2Cl_2$). Purification was completed through preparative HPLC to yield 0.05g of 4-[[5-bromo-4-chloro-6-[(4cyano-2,6-dimethylphenyl)amino]-2-pyrimidinyl]amino]benzonitrile (5.0%); mp. 259–260° C. (interm. 25).

EXAMPLE A15

Sequentially 2,4,6-trimethylbenzenamine (0.0022 mol) and N,N-di(methylethyl)-ethanamine (0.0024 mol) were added to a solution of 4-[[(5-bromo-4,6-dichloro)-2-pyrimidinyl]amino]benzonitrile (0.00218 mol) in 1,4-dioxane (10 ml). The tube was sealed and the suspension was heated to 120–130° C. in an oil bath while stirring for 90 hours. The mixture was cooled to room temperature. More N,N-di(methylethyl)-ethanamine (15 ml) was added, and the sample was reheated to 120–130° C. for 64 hours. The reaction was heated at 150° C. for 6 days. The sample was cooled to room temperature. The sample was diluted with ethylacetate and extracted with cold 1M NaOH. The aqueous phase was backwashed with ethylacetate. The combined organic phases were dried and concentrated. Flash column chromatography over silica gel (eluent: $CH_2Cl_2$). The sample was further purified by preparatory HPLC to yield 0.53 g of 4-[[5-bromo-4-chloro-6-[(2,4,6-trimethylphenyl)amino]-2-pyrimidinyl]amino]benzonitrile (54.9%); mp. 220–221° C. (interm. 26).

EXAMPLE A16

A mixture of 4-aminobenzonitrile (0.0043 mol) and

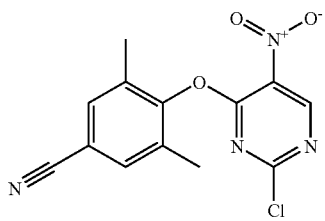

(0.0021 mol) in 1,4-dioxane (30 ml) was stirred at 100° C. for 16 hours. The solvent was removed by rotary evaporation. The solid residue was triturated and the residue was dried in vacuo at 40° C. for 16 hours, yielding 0.452 g of

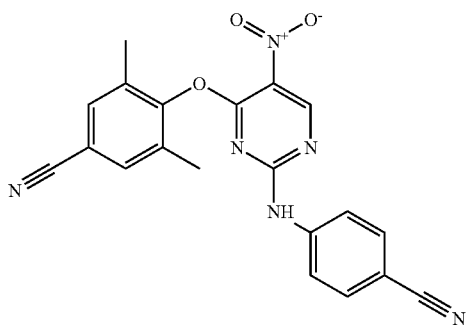

(55%); mp. >300° C. (interm. 27).

EXAMPLE A17

To a pressure vessel was added

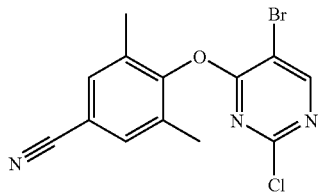

(0.00567 mol), 4-aminobenzonitrile (0.01163 mol) and 1-methyl-2-pyrrolidinone (20 ml). The reaction mixture was heated at 140° C. for 16 hours. The reaction mixture was cooled to room temperature and acetonitrile and water were added. The resulting precipitate was filtered, and the solid recrystallized with acetonitrile to give 1.27 g of 4-[[5-bromo-4-(4-cyano-2,6-dimethylphenoxy)-6-methyl-2-pyrimidinyl]amino]benzonitrile (52); mp. 260–262° C. (interm. 28).

EXAMPLE A18

Intermediate (11) (0.001 mol) and 2,6-dimethyl-4-aminobenzonitrile (0.00473 mol) were combined and heated to 150° C. while stirring for 16 hours. The sample was dissolved in $CH_3OH$ and evaporated onto silica gel (1 g) and eluted with 1:1 hexane: $CH_2Cl_2$, 4:1 $CH_2Cl_2$:hexane, and neat $CH_2Cl_2$ (2 L). The desired fractions were evaporated and the residue was dried in vacuo for 16 hours at 45° C. The thus obtained residue was transferred to a 4 ml vial in $CH_2Cl_2$ and the solvent was evaporated, yielding 0.120 g of 4-[[5-bromo-6-[(4-cyano-2,6-dimethylphenyl)amino]-2-pyrimidinyl]amino]benzonitrile (28.6%); mp. 277–280° C. (interm. 29).

EXAMPLE A19

4-[[5-bromo-4-(4-cyano-2,6-dimethylphenoxy)-6-chloro-2-pyrimidinyl]amino]-benzonitrile (0.00250 mol) and $NH_3$/1,4-dioxane 0.5M (0.015 mol) were heated in a pressure vessel at 150° C. for 4 days. The sample was allowed to sit at ambient conditions for 2 days. Water was added slowly to the mixture until a precipitate formed. The mixture was stirred for 2 hours and filtered. The solid was recrystallized from $CH_3CN$ to obtain 0.58 g (fraction 1). The filtrate was evaporated (fraction 2). Both fractions were combined and purified by column chromatography, eluting with $CH_2Cl_2$. The resulting residue of the desired fraction was recrystallized from $CH_3CN$ to yield 0.44 g of 4-[[4-amino-5-bromo-6-(4-cyano-2,6-dimethylphenyloxy)-2-pyrimidinyl]amino]benzonitrile (40.5%). The sample was dried at 80° C. for 16 hours at 0.2 mm Hg (interm. 30). 4-[[4-amino-5-chloro-6-(4-cyano-2,6-dimethylphenyloxy)-2-pyrimidinyl]amino]benzonitrile (interm. 31) was prepared according to an analogous procedure.

EXAMPLE A20

4-[[5-bromo-4-(4-cyano-2,6-dimethylphenoxy)-6-chloro-2-pyrimidinyl]amino]-benzonitrile (0.000660 mol), tetrahydrofuran (1 ml), and 1-pyrrolidineethanamine (0.00198 mol) were added to a pressure vessel. The mixture was heated at 75° C. for 16 hours. $CH_2Cl_2$ was added, and the mixture was washed with water, dried, filtered and the filtrate was evaporated. Purification using flash column chromatography eluting with 1:9 methanol:methylene chloride produced a solid which was redissolved in CH$_3$CN. HCl/diethylether 1.0M (0.48 ml) was added, and the mixture was cooled in ice. Filtration yielded 0.19 g of 4-[[5-bromo-4-(4-cyano-2,6-dimethylphenoxy)-6-[(1-pyrrolidinyl)ethylamino]-2-pyrimidinyl]amino]benzonitrile hydrochloride (1:1) (50.6%); mp. 208–210° C. (interm. 32).

EXAMPLE A21

To a pressure vessel was added 4-[[5-bromo-4-(4-cyano-2,6-dimethylphenoxy)-6-chloro-2-pyrimidinyl]amino]benzonitrile (0.00064 mol), tetrahydrofuran (3 ml), O-methylhydroxylamine (0.06 g), tetrahydrofuran and NaOH 1N (0.00067 mol). The reaction mixture was stirred for 3 days at room temperature, then for 1 day at 75° C., for 1 day at 90° C. and for 2 days at 110° C. To O-methylhydroxylamine (0.60 g) was added tetrahydrofuran (4 ml) and NaOH 50% (0.00719 mol). The liquid was decanted into the reaction flask and the reaction mixture was heated at 110° C. for 3 days. The solvent was evaporated. The residue was dissolved in CH$_2$Cl$_2$, washed with a saturated NaHCO$_3$ solution and water, dried (Na$_2$SO$_4$), filtered and the solvent was evaporated. The residue was purified by column chromatography over silica gel (eluent: CH$_2$Cl$_2$/CH$_3$OH 98/2). The pure fractions were collected and the solvent was evaporated. The residue was crystallized from CH$_3$CN, filtered off and dried, yielding 0.15 g of 4-[[5-bromo-4-(4-cyano-2,6-dimethylphenoxy)-6-(methoxyamino)-2-pyrimidinyl]amino]benzonitrile (51%); mp. 185–186° C. The sample was dried (0.2 mm Hg, 80° C., 16 hours) (interm. 33).

EXAMPLE A22

A mixture of of 4-[[5-amino-4-(4-cyano-2,6-dimethylphenoxy)-2-pyrimidinyl]amino]-benzonitrile (0.00147 mol) in ethanoic acid anhydride (10 ml) and 2-propanone (10 ml) was stirred at room temperature for 16 hours. The mixture was then heated to 55° C., and more ethanoic acid anhydride (3 ml) was added. The mixture was removed from heat after 18 hours and stirred for 6 days at room temperature. The sample was concentrated by rotary evaporation to a solid. Purification by column chromatography (eluting with 0, 0.5, 1, 1.5, 2% (10% NH$_4$OH in CH$_3$OH) in methylene chloride) yielded;

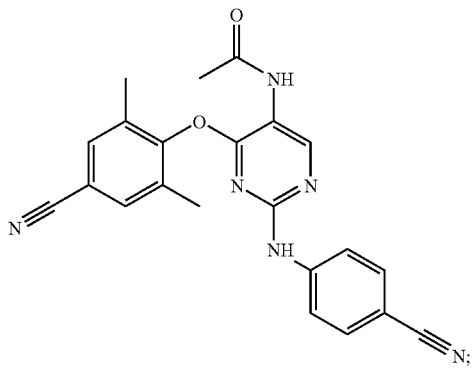

mp. 290–295° C. The solid was dried in vacuo for 16 hours at 60° C. (interm. 34).

EXAMPLE A23

A mixture of 4-[[4-(4-cyano-2,6-dimethylphenoxy)-5-nitro-2-pyriridinyl]amino]-benzonitrile (0.0005 mol) in tetrahydrofuran (20 ml) was hydrogenated overnight with Pd/C 10% (0.100 g) as a catalyst. After uptake of H$_2$ (3 equiv; 0.0015 mol), the catalyst was filtered off and the filtrate was concentrated by rotary evaporation and dried in vacuo over 16 hours at 40° C., yielding 0.15 g of 4-[[5-amino4-(4-cyano-2,6-dimethylphenoxy)- 2-pyrimidinyl]amino]benzonitrile (84%); mp. >300° C. (interm. 35).

EXAMPLE A24

4-[[4-[(2,4,6-trimethylphenyl)amino]-5-nitro-2-pyrimidinyl]amino]benzonitrile (0.001 mol), Pd/C 10% (0.025 g), ethanol (20 ml), and hydrazine (0.030 mol) were combined to form a slurry and stirred at room temperature for 16 hours. The solvent was removed by rotary evaporation. The residue was taken up in tetrahydrofuran (20 ml) and methanol (1 ml). A second portion of hydrazine (0.5 g) was added, and the reaction was stirred for 16 hours at room temperature. A third portion of hydrazine (0.5 ml) was added and the reaction was stirred for an additional 16 hours at room temperature. The sample was concentrated by rotary evaporation onto silica gel (1 g) and purified by flash chromatography (eluent: 0.5, 1,2% 10% (NH$_4$OH in CH$_3$OH) in CH$_2$Cl$_2$). The desired fractions were purified by preparatory HPLC to yield 0.24 g of 4-[[5-amino-4-[(2,4,6-trimethylphenyl)amino]-2-pyrimidinyl]amino]benzonitrile (70%); mp. 224–225° C. (interm. 36).

EXAMPLE A25

Intermediate (15) (0.001 mol), trimethyl silaneacetylene (0.0012 mol), Pd(PPh$_3$)$_2$Cl$_2$ (0.020 g), CuI (0.010 g) and CF$_3$COOH/H$_2$O (3 ml) were combined in a sealed tube and heated to 110° C. for 10 hours. Second portions of the catalysts Pd(PPh$_3$)$_2$Cl$_2$ (0.020 g) and CuI (0.010 g), and CF$_3$COOH/H$_2$O (3 ml) were added and the reaction mixture was stirred for 10 hours at 110° C. The material was concentrated by rotary evaporation. The residue was purified by preparative reversed-phase HPLC. The desired fractions were concentrated and purified by reversed-phase preparative HPLC and dried with a stream of N$_2$, then in vacuo at 40° C. for 16 hours. Yield: 0.011 g of 4-[[5-ethynyl-4-[(2,4,6-trimethylphenyl)amino]-2-pyrimidinyl]amino]benzonitrile; mp. 165–175° C. (interm. 37).

EXAMPLE A26

Intermediate (15) (0.000906 mol), tributylphenyl stannane (0.000906 mol), Pd(PPh$_3$)$_4$ (0.002718 mol), and 1,4-dioxane (3 ml) were combined under N$_2$ in a sealed tube and heated to 110° C. for 16 hours. The reaction mixture was cooled and concentrated by rotary evaporation. The sample was purified by Preparatory Reverse Phase HPLC, then dried under argon stream. Drying in vacuo yielded 0.0845 g of or 4-[[5-phenyl-4-[(2,4,6-trimethylphenyl)amino]-2-pyrimidinyl]amino]benzonitrile; mp. 209–214° C. (interm. 38).

EXAMPLE A27

Intermediate (15) (0.001 mol), tetraethenyl stannane (0.22 ml), 1,4-dioxane (2 ml) and Pd(PPh$_3$)$_4$ (0.112 g) were combined in a sealed tube under argon. The mixture was stirred and heated to 100° C. for 16 hours. More tetraethenyl stannane and Pd(PPh$_3$)$_4$ were added. The reaction was placed under argon, stirred and heated. The reaction was concentrated by rotary evaporation and purified on preparative HPLC. The material was dried with a N$_2$ stream, and dried under vacuum for 4 hours at 60° C. to obtain 0.422 g of 4-[[5-ethenyl-4-[(2,4,6-trimethylphenyl)amino]-2-pyrimidinyl]-amino]benzonitrile; mp. 237–242° C. (interm. 39).

EXAMPLE A28

Intermediate (15) (0.001225 mol), CuCN (0.001470 mol) and N,N-dimethylformamide (2 ml) were combined in a sealed tube under argon, then stirred and heated to 160° C. for 16 hours. The residue was purified by column chromatography (eluent: CH$_2$Cl$_2$/hexane 1/1, then pure CH$_2$Cl$_2$). The desired fractions were collected and the solvent was evaporated. The residue was triturated under CH$_2$Cl$_2$ at room temperature. The solid was dried (vacuum, 40° C., 24 hours, yielding 0.0864 g of

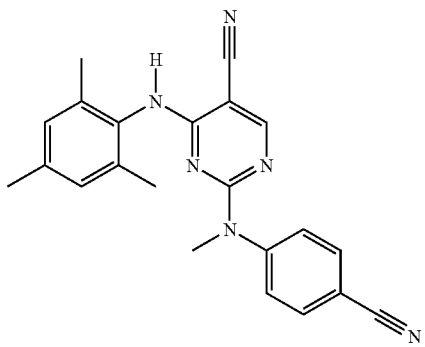

(24%); mp. 254–259° C. (interm. 40).

B. Preparation of the Final Prodrugs

EXAMPLE B 1 a) The preparation of

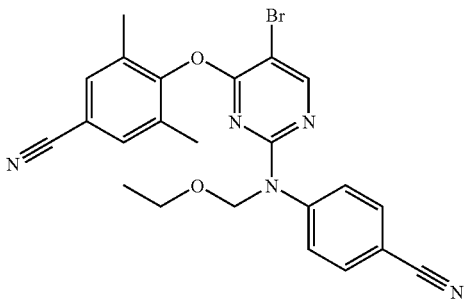

(compound 1)

To a flask under argon was added NaH 60% and tetrahydrofuran. The reaction was stirred at room temperature for 10 minutes and intermediate (22) was added. After stirring for 1 hour (chloromethoxy)ethane was added. The reaction mixture was stirred at room temperature for another 16 hours and the solvent was evaporated to give 2.76 g of a white solid. The solid was dissolved in acetonitrile/methylene chloride and evaporated onto 36 g of silica gel. A flash chromatography eluting with 10% and 20% ethyl acetate: hexane gave a white solid. The solid was dissolved in methylene chloride and chromatographed on silica gel eluting with 1:1 and 2:1 CH$_2$Cl$_2$:hexane. One recrystallization with acetonitrile gave 0.47 g (19%) of compound 1 as a white solid; mp. 181–182° C.

b) The preparation of

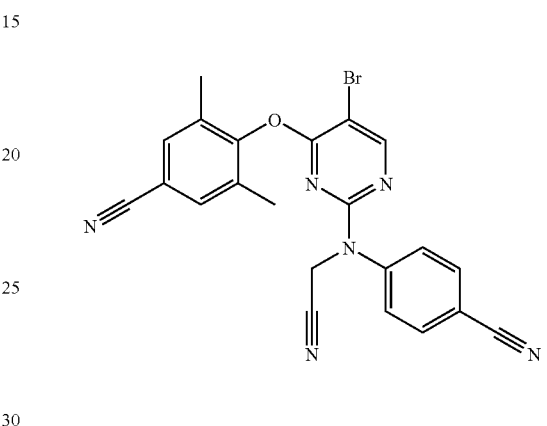

(compound 2)

n-Butyl lithium (0.010 mol) was added to a solution of N-(1-methylethyl)-2-propanamine (0.010 mol) in tetrahydrofuran (300 ml), stirred at 0° C. After stirring cold for 30 minutes,

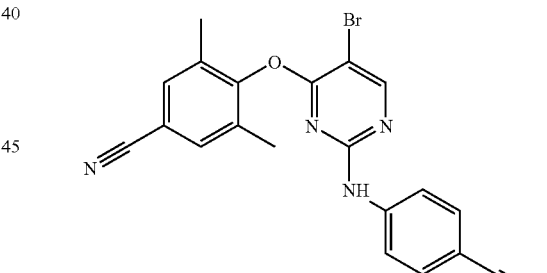

(interm. 22) (0.005 mol) was added. The resulting mixture was stirred cold for 15 minutes at which point bromoacetonitrile (0.015 mol) was added and the temperature was allowed to rise to room temperature and the reaction mixture was stirred for 3 days which drove the reaction to 50% completion. Quenched with 0.5 ml H$_2$O, the sample was concentrated by rotary evaporation onto silica gel, and purified by flash chromatography (Biotage Flash 40M, eluting with 0, 0.5, 1% (10% NH$_4$OH in CH$_3$OH) in CH$_2$Cl$_2$). Preparatory HPLC purification eluting into tubes containing 1 mmol NaHCO$_3$ effected final purification. Lyophilized material was taken up in water/CH$_2$Cl$_2$ (1:1 50 ml total) and separated. The aqueous layer was extracted 2 more times with 25 ml CH$_2$Cl$_2$. The organic layers were combined and dried over sodium sulfate and rotary evaporated to white solid dried in vacuo at 65° C. for 18 hours. Yield: 0.10 g (9%) of compound 2; mp. 205–210° C.

EXAMPLE B2

The preparation of

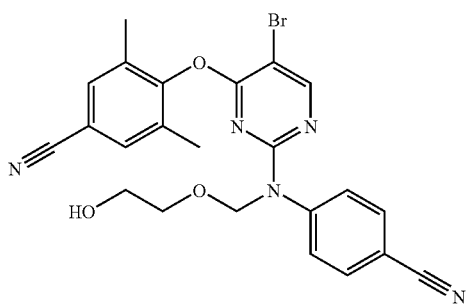

(compound 3)

To a homogeneous solution of

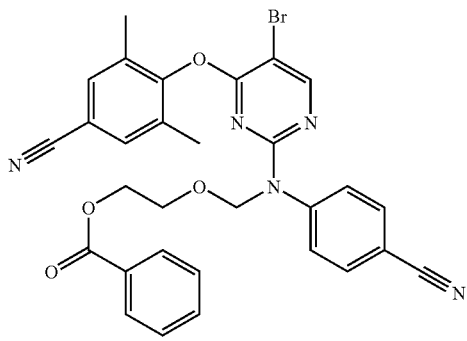

(0.00162 mol), prepared according to Example B1a, tetrahydrofuran (8 ml) and H$_2$O (2 ml), was added LiOH.H$_2$O (0.00178 mol). The reaction mixture was stirred at room temperature for 4 days, the solvent evaporated, the solid dissolved in methylene chloride, the solution filtered and the filtrate chromatographed on silica gel eluting with 0 and 1% methanol: methylene chloride to give 0.87 g of a white solid. Two re-crystallizations with acetonitrile gave 0.39 g (48.7%) of compound 3; mp. 199–200° C.

EXAMPLE B3

The preparation of

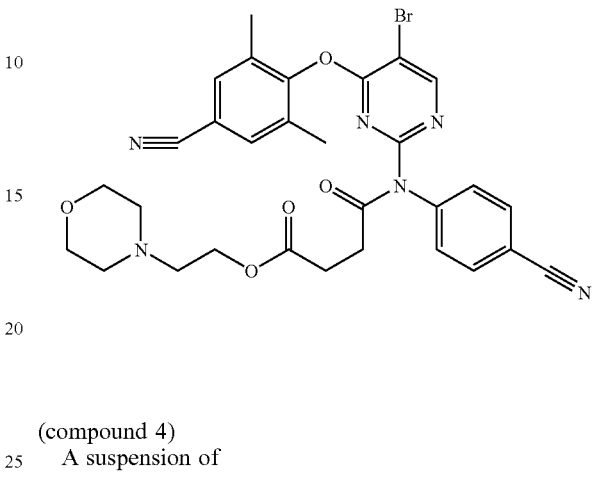

(compound 4)

A suspension of (interm. 22) (0.0020 mol) in N,N-dimethylformamide (40 ml) was treated with 0.24 g NaH in one portion. The effervescent mixture was stirred for 90 minutes to yield a bright yellow suspension. A mixture of Cl—C(=O)—(CH$_2$)$_2$—C(=O)—Cl (0.020 mol) in N,N-dimethylformamide (10 ml) was prepared at –60° C. in a dry ice/2-propanol bath. Via cannula, the resultant of the above suspension was transferred to the cold solution of Cl—C(=O)—(CH$_2$)$_2$—C(=O)—Cl dropwise over 20 minutes. The mixture was warmed to room temperature and stirred for 3 days. The reaction mixture was cooled in an ice bath and 4-morpholine ethanol (0.063 mol) was added dropwise over 15 minutes. The reaction mixture was returned to room temperature and after 18 hours poured into ether and treated with saturated NaHCO$_3$. The layers were separated and the aqueous fraction was extracted 3 times with ether and the combined ether extracts were backwashed 5 times with water and dried over MgSO$_4$. Concentration yielded 1.07 g of a waxy residue that was subjected to reverse phase preparative HPLC. Lyophilization of the appropriate fractions provided 0.14 g (9.4%) of compound 4; mp. 84–85° C.

Table 1 lists the compounds that were prepared according to one of the above Examples.

TABLE 1

[Structure: 4-[[5-bromo-2-[(4-cyanophenyl)(R¹)amino]pyrimidin-4-yl]oxy]-3,5-dimethylbenzonitrile core, with R¹ substituent on the N]

| Co No. | Ex. No. | R¹ | Physical data (mp. in ° C.) |
|---|---|---|---|
| 1 | B1a | ethoxymethyl | 181–182 |
| 5 | B1a | C₆H₅-C(=O)-O-CH₂CH₂-O-CH₂CH₃ (2-ethoxyethyl benzoate group) | 144–145 |
| 6 | B1a | octyloxymethyl | 115–116 |
| 7 | B1a | 2-methoxyethoxymethyl | 99–100 |
| 8 | B1a | (1-methyl-1H-imidazol-4-yl)sulfonyl | 269–272 |
| 9 | B1a | methylsulfonyl | 195–196 |
| 10 | B1a | phenylsulfonyl | 211–214 |
| 11 | B1a | [4-(trifluoromethyl)phenyl]sulfonyl | 239–241 |
| 12 | B1a | 1-oxooctyl | 137–138 |
| 2 | B1b | cyanomethyl | 205–210 |
| 3 | B2 | 2-hydroxyethoxymethyl | 199–200 |
| 4 | B3 | morpholino-CH₂CH₂-O-C(=O)-CH₂CH₂-C(=O)-CH₃ | 84–85 |
| 13 | B3 | (CH₃)₂N-CH₂CH₂-O-C(=O)-CH₂CH₂-C(=O)-CH₃ | 112–114 |
| 14 | B3 | (CH₃)₂N-CH₂CH₂-N(CH₃)-CH₂CH₂-O-C(=O)-CH₂CH₂-C(=O)-CH₃ | 112–114 |

C. Pharmacological Example

The pharmacological activity of the present compounds was examined using the following tests.

EXAMPLE C.1

The metabolism of the present compounds was studied in subcellular liver fractions (1200×g) of rat, dog or human. The compounds were incubated at a final protein concentration of 30 μM; incubations were performed up to 120 minutes at a final protein concentration equivalent to 1 mg/ml microsomal proteins. Reactions were stopped by the addition of an equal volume (2 ml) of N,N-dimethylsulfoxide. Samples were stored at ≦−18° C. until analysis. The anti-HIV activity ($IC_{50}$) of the incubates was determined by the assay described below as Example C.2 and the anti-HIV activity after incubation was compared with said activity prior to incubation (also determined with the assay described below). Table 2 lists $IC_{50}$ values prior to and after incubation in subcellular liver fractions.

EXAMPLE C.2

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in µM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in µM).

TABLE 2

| Comp. No. | $IC_{50\ before}$ (µM) | Incubation medium/time | $IC_{50\ after}$ (µM) |
| --- | --- | --- | --- |
| 5 | >1.000 | Rat/120 minutes | 0.423 |
| 5 | >1.000 | Dog/120 minutes | 0.785 |
| 3 | >1.000 | Dog/120 minutes | 0.809 |
| 1 | >1.000 | Dog/120 minutes | 0.138 |
| 1 | >1.000 | Rat/120 minutes | 0.175 |
| 1 | >1.000 | Human/30 minutes | 0.293 |
| 1 | >1.000 | Human/120 minutes | 0.165 |

What is claimed is:

1. A compound of formula $$(A_1)(A_2)N-R^1 \quad (I)$$

an N-oxide form, a pharmaceutically acceptable addition salt, a quaternary amine or a stereochemically isomeric form thereof, wherein $R^1$ is $C_{1-6}$alkyl substituted with at least one of cyano, amino, mono- or di($C_{1-4}$alkyl)amino, nitro, $C_{1-12}$alkyloxy, hydroxy$C_{1-12}$alkyloxy, $C_{1-6}$alkyloxy$C_{1-12}$alkyloxy, $C_{1-6}$alkylcarbonyloxy$C_{1-12}$alkyloxy, aryl$^1$carbonyloxy$C_{1-12}$alkyloxy or Het$^1$carbonyloxy$C_{1-12}$alkyloxy; —S(=O)—$R^8$; —(=O)$_2$—$R^8$; $C_{7-12}$alkylcarbonyl; $C_{1-6}$alkyloxycarbonyl$C_{1-6}$alkylcarbonyl; hydroxycarbonyl-$C_{1-6}$alkylcarbonyl; aryl$^1$$C_{1-6}$alkyloxycarbonyl$C_{1-6}$alkylcarbonyl; Het$^1$$C_{1-6}$alkyloxycarbonyl-$C_{1-6}$alkylcarbonyl; or $R^9R^{10}N$—$C_{1-6}$alkyloxycarbonyl-$C_{1-6}$alkylcarbonyl;

$(A_1)(A_2)N$— is the covalently bonded form of the corresponding intermediate of formula $(A_1)(A_2)N$—H, wherein said intermediate of formula $(A_1)(A_2)N$—H is a pyrimidine of formula

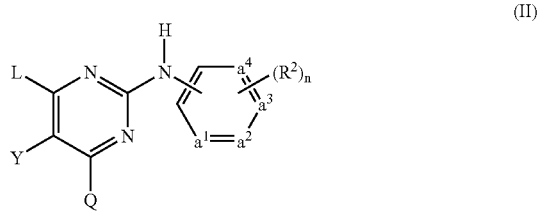

(II)

an N-oxide, a pharmaceutically acceptable addition salt, a quatemary amine or a stereochemically isomeric form thereof, wherein -$a^1$=$a^2$-$a^3$=$a^4$- is a bivalent radical of formula —CH=CH—CH=CH— (a-1);

n is 0, 1, 2, 3, or 5;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, aminocarbonyl, nitro, amino, mono- or di($C_{1-6}$alkyl)amino, polyhalomethyl, polyhalomethyloxy, polyhalomethylthio, —(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

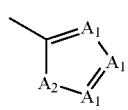

(c)

wherein each $A_1$ independently is N, CH or CR$^6$; and $A_2$ is NH, O, S or NR$^6$;

L is $C_{1-10}$alkyl, $C_{2-10}$alkenyl, $C_{2-10}$alkynyl, or $C_{3-7}$cycloalkyl, wherein each of said groups is substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined for $R^2$; or L is —$X^1$—$R^3$ or —$X^2$-Alk-$R^{11}$ wherein Alk is $C_{1-4}$alkanediyl;

$R^3$ and $R^{11}$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ and $X^2$ each independently are —NR$^7$—, —NH—NH—, —N=N—, —O—, —C(=O)—, —CHOH—, —S—, —S(=O)— or —S(=O)$_2$—;

Q is hydrogen, $C_{1-6}$alkyl, halo, polyhalo$C_{1-6}$alkyl or —NR$^4$R$^5$;

$R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, $C_{1-12}$alkylthiocarbonyl, aryl, amino, mono- or di($C_{1-12}$alkyl)amino, mono- or di($C_{1-2}$alkyl)aminocarbonyl wherein each of the aforementioned $C_{1-2}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$R$^{12}$, —NH—S(=O)

$_pR^{12}$, —C(=O)$R^{12}$, —NHC(=O)H, —C(=O)NHNH$_2$, —NHC(=O)$R^{12}$, —C(=NH)$R^{12}$, aryl and Het; or $R^4$ and $R^5$ taken together may form pyrrolidinyl, piperidinyl, morpholinyl, azido or mono- or di($C_{1-12}$alkyl)amino$C_{1-4}$alkanediyl;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;

$R^8$ is $C_{1-6}$alkyl, aryl$^1$ or Het$^1$;

$R^9$ and $R^{10}$ each independently are selected from hydrogen, $C_{1-4}$alkyl, amino$C_{1-4}$alkyl, or mono- or di($C_{1-4}$alkyl)amino$C_{1-4}$alkyl; or $R^9$ and $R^{10}$ are taken together to form a bivalent radical of formula —CH$_2$—CH$_2$-Z-CH$_2$—CH$_2$— with Z being O, NR$^{13}$, CH$_2$, or a direct bond;

$R^{12}$ is methyl, amino, mono- or dimethylamino or polyhalomethyl;

$R^{13}$ is hydrogen, $C_{1-4}$alkyl, amino$C_{1-4}$alkyl, or mono- or di($C_{1-4}$alkyl)amino$C_{1-4}$alkyl;

$R^{14}$ is methyl, amino, mono- or dimethylamino or polyhalomethyl;

Y is hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^{14}$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^{14}$, —NH—S(=O)$_p$R$^{14}$, —C(=O)$R^{14}$, —NHC(=O)H, —C(=O)NHNH$_2$, —NHC(=O)$R^{14}$, —C(=NH)$R^{14}$ or aryl;

p is 1 or 2;

aryl$^1$is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, amino, mono- or di($C_{1-4}$alkyl)amino, polyhalo$C_{1-6}$alkyl and polyhalo$C_{1-6}$alkyloxy;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het$^1$ is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl; said partially saturated heterocyclic radical is selected from imidazolinyl, pyrazolinyl, pyrrolinyl, 4,5-dihydro-oxazolyl, 4,5-dihydro-thiazolyl, dihydrofuranyl, and dihydrothienyl; and said aromatic heterocyclic radical is selected from pyrrolyl, furanyl, thienyl, imidazolyl, oxazolyl, thiazolyl, pyridyl, pyrimidinyl, pyrazinyl and pyridazinyl wherein each of said aromatic heterocyclic radicals may optionally be substituted with $C_{1-4}$alkyl;

Het is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl wherein each of said saturated heterocyclic radicals may optionally be substituted with an oxo group; said partially saturated heterocyclic radical is selected from imidazolinyl, pyrazolinyl, pyrrolinyl, 4,5-dihydro-oxazolyl, 4,5-dihydro-thiazolyl, dihydrofuranyl, and dihydrothienyl; and said aromatic heterocyclic radical is selected from pyrrolyl, furanyl, thienyl, pyridyl, pyrimidinyl, pyrazinyl and pyridazinyl wherein each of said aromatic heterocyclic radicals may optionally be substituted with hydroxy;

provided that acetonitrile, [[2-bromo-4-(1-methylethyl)phenyl](4,6-dimethyl-2-pyrimidinyl)-amino]-; acetonitrile, [[2-bromo-4-(1-methylethyl)phenyl](4,6-dimethyl-2-pyrimidinyl)amino]-, monohydrochloride; 1,2-ethanediamine, N-[2-bromo-4-(1-methylethyl)phenyl]-N-(4,6-dimethyl-2-pyrimidinyl)-N',N'-diethyl; and 1,2-ethanediamine, N-[2-bromo-4-(1-methylethyl)phenyl]-N-(4,6-dimethyl-2-pyrimidinyl)-N',N'-dimethyl are not included.

2. A compound of claim 1, wherein the ($A_1$)($A_2$)N-moiety is the covalently bonded form of the corresponding intermediate of formula ($A'_1$)($A'_2$)N—H, said compound being represented by formula ($A'_1$)($A'_2$)N—$R^1$ (I') wherein said corresponding intermediate of formula ($A'_1$)($A'_2$)N—H is a pyrimidine of formula

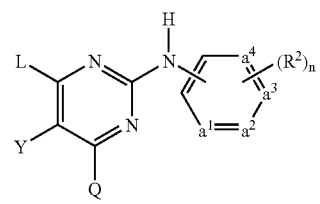

(II)

an N-oxide, an addition salt, a quaternary amine or a stereochemically isomeric form thereof, wherein -$b^1$=$b^2$-C($R^{2a}$)=$b^3$-$b^4$= is a bivalent radical of formula —CH=CH—C($R^{2a}$)=CH—CH=    (b-1);

q is 0, 1, or 2; or where possible q is 3 or 4;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^6$, —NH—S(=O)$_p$R$^6$, —C(=O)$R^6$, —NHC(=O)H, —C(=O)NHNH$_2$, —NHC(=O)$R^6$, —C(=NH)$R^6$ or a radical of formula

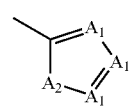

(c)

wherein each $A_1$ independently is N, CH or CR$^6$; and $A_2$ is NH, O, S or NR$^6$;

p is 1 or 2; and $R^6$ is methyl, amino, mono- or dimethylamino or polyhalomethyl.

3. A compound of claim 1, wherein $R^1$ is $C_{1-6}$alkyl substituted with cyano, $C_{1-12}$alkyloxy, hydroxy$C_{1-12}$alkyloxy, $C_{1-6}$alkyloxy$C_{1-12}$alkyloxy or aryl$^1$ carbonyloxy-$C_{1-12}$alkyloxy; —(=O)$_2$—R$^8$ with R$^8$ being $C_{1-6}$alkyl, aryl$^1$ or Het$^1$; $C_{7-12}$alkylcarbonyl; R$^9$R$^{10}$N-C$_{1-6}$alkyloxycarbonylC$_{1-6}$alkylcarbonyl with R$^9$ and R$^{10}$ each independently being selected from $C_{1-4}$alkyl, mono- or di($C_{1-4}$alkyl)amino$C_{1-4}$alkyl, or R$^9$ and R$^{10}$ are taken together to form a bivalent radical of formula —CH$_2$—CH$_2$—O—CH$_2$—CH$_2$—.

4. A compound of claim 1, wherein L is —X—R$^3$ wherein R$^3$ is 2,4,6-trisubstituted phenyl.

5. A compound of claim 1, wherein Y is hydrogen, cyano, —C(=O)NH$_2$ or halo.

6. A compound of claim 1, wherein Q is hydrogen or NR$^4$R$^5$.

7. A compound of claim 1, wherein -a$^1$=a$^2$-a$^3$=a$^4$- is a bivalent radical of formula —CH=CH—CH=CH— (a-1), R$^2$ is 4-cyano, and n is 1.

8. A compound of claim 1, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino[ -2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

9. A compound of claim 2, wherein $R^1$ is $C_{1-6}$alkyl substituted with at least one of cyano, $C_{1-12}$alkyloxy, hydroxy$C_{1-12}$alkyloxy, $C_{1-6}$alkyloxy$C_{1-12}$alkyloxy or aryl$^1$ carbonyloxy$C_{1-12}$alkyloxy; —S(=O)$_2$—R$^8$ with R$^8$ being $C_{1-6}$alkyl, aryl$^1$ or Het$^1$; $C_{7-12}$alkylcarbonyl; R$^9$R$^{10}$N—C$_{1-6}$alkyloxycarbonylC$_{1-6}$alkylcarbonyl with R$^9$ and R$^{10}$ each independently being selected from $C_{1-4}$alkyl, mono- or di($C_{1-4}$alkyl)amino$C_{1-4}$alkyl or R$^9$ and R$^{10}$ are taken together to form a bivalent radical of formula —CH$_2$—CH$_2$—O—CH$_2$—CH$_2$—.

10. A compound of claim 2, wherein L is —X$^1$—R$^3$ wherein R$^3$ is 2,4,6-trisubstituted phenyl.

11. A compound of claim 3, wherein L is —X$^1$—R$^3$ wherein R$^3$ is 2,4,6-trisubstituted phenyl.

12. A compound of claim 9, wherein L is —X$^1$—R$^3$ wherein R$^3$ is 2,4,6-trisubstituted phenyl.

13. A compound of claim 2, wherein Y is hydrogen, cyano, —C(=O)NH$_2$ or halo.

14. A compound of claim 3, wherein Y is hydrogen, cyano, —C(=O)NH$_2$ or halo.

15. A compound of claim 9, wherein Y is hydrogen, cyano, —C(=O)NH$_2$ or halo.

16. A compound of claim 4, wherein Y is hydrogen, cyano, —C(=O)NH$_2$ or halo.

17. A compound of claim 10, wherein Y is hydrogen, cyano, —C(=O)NH$_2$ or halo.

18. A compound of claim 11, wherein Y is hydrogen, cyano, —C(=O)NH$_2$ or halo.

19. A compound of claim 12, wherein Y is hydrogen, cyano, —C(=O)NH$_2$ or halo.

20. A compound of claim 2, wherein Q is hydrogen or NR$^4$R$^5$.

21. A compound of claim 3, wherein Q is hydrogen or NR$^4$R$^5$.

22. A compound of claim 9, wherein Q is hydrogen or NR$^4$R$^5$.

23. A compound of claim 4, wherein Q is hydrogen or NR$^4$R$^5$.

24. A compound of claim 10, wherein Q is hydrogen or NR$^4$R$^5$.

25. A compound of claim 11, wherein Q is hydrogen or NR$^4$R$^5$.

26. A compound of claim 12, wherein Q is hydrogen or NR$^4$R$^5$.

27. A compound of claim 5, wherein Q is hydrogen or NR$^4$R$^5$.

28. A compound of claim 13, wherein Q is hydrogen or NR$^4$R$^5$.

29. A compound of claim 14, wherein Q is hydrogen or NR$^4$R$^5$.

30. A compound of claim 15, wherein Q is hydrogen or NR$^4$R$^5$.

31. A compound of claim 16, wherein Q is hydrogen or NR$^4$R$^5$.

32. A compound of claim 17, wherein Q is hydrogen or NR$^4$R$^5$.

33. A compound of claim 18, wherein Q is hydrogen or NR$^4$R$^5$.

34. A compound of claim 19, wherein Q is hydrogen or NR$^4$R$^5$.

35. A compound of claim 2, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

36. A compound of claim 3, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

37. A compound of claim 9, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

38. A compound of claim 4, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

39. A compound of claim 10, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

40. A compound of claim 4, wherein the intermediate of formula (II) or (II') is one of 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

41. A compound of claim 12, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

42. A compound of claim 5, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

43. A compound of claim 13, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

44. A compound of claim 14, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano- 2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

45. A compound of claim 15, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

46. A compound of claim 16, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

47. A compound of claim 17, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

48. A compound of claim 18, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

49. A compound of claim 19, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

50. A compound of claim 6, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quaternary amine and a stereochemically isomeric form thereof.

51. A compound of claim 20, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5- dimethylbenzonitrile; or an N-oxide, an addition salt, a quatemary amine and a stereochemically isomeric form thereof.

52. A compound of claim 21, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

53. A compound of claim 22, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

54. A compound of claim 23, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

55. A compound of claim 24, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

56. A compound of claim 25, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

57. A compound of claim 26, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

58. A compound of claim 27, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

59. A compound of claim 28, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano- 2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

60. A compound of claim 29, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

61. A compound of claim 30, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

62. A compound of claim 31, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

63. A compound of claim 32, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

64. A compound of claim 33, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

65. A compound of claim 34, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

66. A compound of claim 35, wherein the intermediate of formula (II) or (II') is 4-[[4-amino-5-chloro-6-[(2,4,6-trimethylphenyl)amino]-2-pyrimidinyl]amino]benzonitrile; 4-[[5-chloro-4-[(2,4,6-trimethylphenyl)amino]-2-pyrimidinyl]amino]benzonitrile; 4-[[5-bromo-4-(4-cyano-2,6-dimethylphenoxy)-2-pyrimidinyl]amino]benzonitrile; 4-[[4-amino-5-chloro-6-[(4-cyano-2,6-dimethylphenyl)amino]-2-pyrimidinyl]amino]benzonitrile; 4-[[5-bromo-6-[(4-cyano-2,6-dimethylphenyl)amino]-2-pyrimidinyl]amino]benzonitrile; 4-[[4-amino-5-chloro-6-(4-cyano-2,6-dimethylphenyloxy)-2-pyrimidinyl]amino]benzonitrile; 4-[[4-amino-5-bromo-6-(4-cyano-2,6-dimethylphenyloxy)-2-pyrimidinyl]amino]benzonitrile; 4-[[4-[(2,4,6-trimethylphenyl)amino]-2-pyrimidinyl]amino]benzonitrile; or 4-[[2-[(4-cyanophenyl)amino]-4-pyrimidinyl]amino]-3,5-dimethylbenzonitrile; or an N-oxide, an addition salt, a quatemary amine and a stereochemically isomeric form thereof.

67. A process for preparing a compound of claim 1, comprising:
a) reacting an intermediate of formula $(A_1)(A_2)N$—H with an intermediate of formula (III) in the presence of a suitable base and a suitable reaction-inert solvent

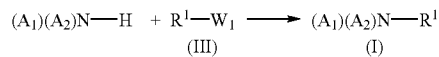

wherein
$W_1$ is a suitable leaving group; and
b) reacting an intermediate of formula $(A_1)(A_2)N$—H with an intermediate of formula (IV), and an intermediate of formula (V) in the presence of a suitable base and a suitable reaction-inert solvent

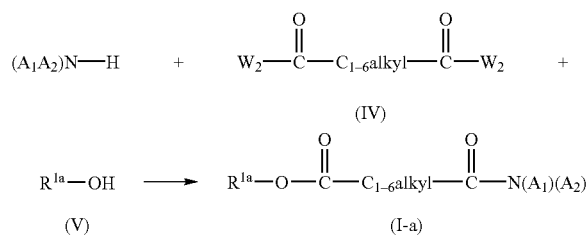

wherein
$W_2$ is a suitable leaving group, and $R^{1a}$ is $C_{1-6}$alkyl, aryl$^1C_{1-6}$alkyl, Het$^1C_{1-6}$alkyl or $R^9R^{10}N$—$C_{1-6}$alkyl.

68. A process of claim 67, further comprising converting compounds of formula (I) into each other.

69. A process of claim 67, further comprising converting compounds of formula (I) into a therapeutically active non-toxic acid addition salt by treatment with an acid.

70. A process of claim 67, further comprising converting compounds of formula (I) into a therapeutically active non-toxic acid addition salt and converting the acid addition salt form into a free base by treatment with alkali.

71. A process of claim 67, further comprising preparing stereochemically isomeric forms or N-oxide forms thereof.

72. A pharmaceutical composition comprising a pharmaceutically acceptable carrier and a therapeutically effective amount of a compound of claim 1.

73. A pharmaceutical composition comprising a pharmaceutically acceptable carrier and as active ingredients (a) a compound of claim 1, and (b) another antiretroviral compound.

74. A pharmaceutical composition comprising a pharmaceutically acceptable carrier and a therapeutically effective amount of a compound of claim 2.

75. A pharmaceutical composition comprising a pharmaceutically acceptable carrier and a therapeutically effective amount of a compound of claim 3.

76. A pharmaceutical composition comprising a pharmaceutically acceptable carrier and a therapeutically effective amount of a compound of claim 4.

77. A pharmaceutical composition comprising a pharmaceutically acceptable carrier and a therapeutically effective amount of a compound of claim 5.

78. A pharmaceutical composition comprising a pharmaceutically acceptable carrier and a therapeutically effective amount of a compound of claim 6.

79. A pharmaceutical composition comprising a pharmaceutically acceptable carrier and a therapeutically effective amount of a compound of claim 7.

80. A pharmaceutical composition comprising a pharmaceutically acceptable carrier and a therapeutically effective amount of a compound of claim 8.

81. A pharmaceutical composition comprising a pharmaceutically acceptable carrier and a therapeutically effective amount of a compound of claim 9.

82. A pharmaceutical composition comprising a pharmaceutically acceptable carrier and a therapeutically effective amount of a compound of claim 12.

83. A pharmaceuticalcomposition comprising a pharmaceutically acceptable carrier and a therapeutically effective amount of a compound of claim 19.

84. A pharmaceutical composition comprising a pharmaceutically acceptable carrier and a therapeutically effective amount of a compound of claim 34.

85. A pharmaceutical composition comprising a pharmaceutically acceptable carrier and a therapeutically effective amount of a compound of claim 65.

86. A pharmaceutical composition comprising a pharmaceutically acceptable carrier and as active ingredients (a) a compound of claim 2, and (b) another antiretroviral compound.

87. A pharmaceutical composition comprising a pharmaceutically acceptable carrier and as active ingredients (a) a compound of claim 3, and (b) another antiretroviral compound.

88. A pharmaceutical composition comprising a pharmaceutically acceptable carrier and as active ingredients (a) a compound of claim 4, and (b) another antiretroviral compound.

89. A pharmaceutical composition comprising a pharmaceutically acceptable carrier and as active ingredients (a) a compound of claim 5, and (b) another antiretroviral compound.

90. A pharmaceutical composition comprising a pharmaceutically acceptable carrier and as active ingredients (a) a compound of claim 6, and (b) another antiretroviral compound.

91. A pharmaceutical composition comprising a pharmaceutically acceptable carrier and as active ingredients (a) a compound of claim 7, and (b) another antiretroviral compound.

92. A pharmaceutical composition comprising a pharmaceutically acceptable carrier and as active ingredients (a) a compound of claim 8, and (b) another antiretroviral compound.

93. A pharmaceutical composition comprising a pharmaceutically acceptable carrier and as active ingredients (a) a compound of claim 12, and (b) another antiretroviral compound.

94. A pharmaceutical composition comprising a pharmaceutically acceptable carrier and as active ingredients (a) a compound of claim 15, and (b) another antiretroviral compound.

95. A pharmaceutical composition comprising a pharmaceutically acceptable carrier and as active ingredients (a) a compound of claim 19, and (b) another antiretroviral compound.

96. A pharmaceutical composition comprising a pharmaceutically acceptable carrier and as active ingredients (a) a compound of claim 22, and (b) another antiretroviral compound.

97. A pharmaceutical composition comprising a pharmaceutically acceptable carrier and as active ingredients (a) a compound of claim 25, and (b) another antiretroviral compound.

98. A pharmaceutical composition comprising a pharmaceutically acceptable carrier and as active ingredients (a) a compound of claim 29, and (b) another antiretroviral compound.

99. A pharmaceutical composition comprising a pharmaceutically acceptable carrier and as active ingredients (a) a compound of claim 38, and (b) another antiretroviral compound.

100. A pharmaceutical composition comprising a pharmaceutically acceptable carrier and as active ingredients (a) a compound of claim 42, and (b) another antiretroviral compound.

101. A pharmaceutical composition comprising a pharmaceutically acceptable carrier and as active ingredients (a) a compound of claim 50, and (b) another antiretroviral compound.

102. A pharmaceutical composition comprising a pharmaceutically acceptable carrier and as active ingredients (a) a compound of claim 66, and (b) another antiretroviral compound.

103. A product containing (a) a compound of claim 1, and (b) another antiretroviral compound, as a combined preparation for simultaneous, separate, or sequential use in the treatment of HIV infection.

104. A product containing (a) a compound of claim 2, and (b) another antiretroviral compound, as a combined preparation for simultaneous, separate or sequential use in the treatment of HIV infection.

105. A product containing (a) a compound of claim 3, and (b) another antiretroviral compound, as a combined preparation for simultaneous, separate or sequential use in the treatment of HIV infection.

106. A product containing (a) a compound of claim 4, and (b) another antiretroviral compound, as a combined preparation for simultaneous, separate or sequential use in the treatment of HIV infection.

107. A product containing (a) a compound of claim 5, and (b) another antiretroviral compound, as a combined preparation for simultaneous, separate or sequential use in the treatment of HIV infection.

108. A product containing (a) a compound of claim 6, and (b) another antiretroviral compound, as a combined preparation for simultaneous, separate or sequential use in the treatment of HIV infection.

109. A product containing (a) a compound of claim 7, and (b) another antiretroviral compound, as a combined preparation for simultaneous, separate or sequential use in the treatment of HIV infection.

110. A product containing (a) a compound of claim 8, and (b) another antiretroviral compound, as a combined preparation for simultaneous, separate or sequential use in the treatment of HIV infection.

111. A product containing (a) a compound of claim 12, and (b) another antiretroviral compound, as a combined preparation for simultaneous, separate or sequential use in the treatment of HIV infection.

112. A product containing (a) a compound of claim 15, and (b) another antiretroviral compound, as a combined preparation for simultaneous, separate or sequential use in the treatment of HIV infection.

113. A product containing (a) a compound of claim 19, and (b) another antiretroviral compound, as a combined preparation for simultaneous, separate or sequential use in the treatment of HIV infection.

114. A product containing (a) a compound of claim 22, and (b) another antiretroviral compound, as a combined preparation for simultaneous, separate or sequential use in the treatment of HIV infection.

115. A product containing (a) a compound of claim 25, and (b) another antiretroviral compound, as a combined preparation for simultaneous, separate or sequential use in the treatment of HIV infection.

116. A product containing (a) a compound of claim 29, and (b) another antiretroviral compound, as a combined preparation for simultaneous, separate or sequential use in the treatment of HIV infection.

117. A product containing (a) a compound of claim 38, and (b) another antiretroviral compound, as a combined preparation for simultaneous, separate or sequential use in the treatment of HIV infection.

118. A product containing (a) a compound of claim 42, and (b) another antiretroviral compound, as a combined preparation for simultaneous, separate or sequential use in the treatment of HIV infection.

119. A product containing (a) a compound of claim 50, and (b) another antiretroviral compound, as a combined preparation for simultaneous, separate or sequential use in the treatment of HIV infection.

120. A product containing (a) a compound of claim 66, and (b) another antiretroviral compound, as a combined preparation for simultaneous, separate or sequential use in the treatment of HIV infection.

121. A method for the treatment of HIV (Human Immunodeficiency Virus) infection, comprising providing an active ingredient and administering an effective amount of a composition comprising said active ingredient to a human being in need thereof, wherein said active ingredient comprises at least one of a compound of formula $$(A_1)(A_2)N\text{—}R^1 \qquad (I)$$

an N-oxide form, a pharmaceutically acceptable addition salt, a quaternary amine and a stereochemically isomeric form thereof, wherein $R^1$ is $C_{1-6}$alkyl substituted with cyano, amino, mono- or di($C_{1-4}$alkyl)amino, nitro, $C_{1-12}$alkyloxy, hydroxy$C_{1-12}$alkyloxy, $C_{1-6}$alkyloxy$C_{1-12}$alkyloxy, $C_{1-6}$alkylcarbonyloxy$C_{1-12}$alkyloxy, aryl$^1$carbonyloxy$C_{1-12}$alkyloxy or Het$^1$carbonyloxy$C_{1-12}$alkyloxy; —S(=O)—R$^8$; —(=O)$_2$—R$^8$; $C_{7-12}$alkylcarbonyl; $C_{1-6}$alkyloxycarbonyl$C_{1-6}$alkylcarbonyl; hydroxycarbonyl$C_{1-6}$alkyl-carbonyl; aryl$^1C_{1-6}$alkyloxycarbonyl$C_{1-6}$alkylcarbonyl; Het$^1C_{1-6}$alkyloxycarbonyl-$C_{1-6}$alkylcarbonyl; or $R^9R^{10}$N—$C_{1-6}$alkyloxycarbonyl$C_{1-6}$alkylcarbonyl;

$(A_1)(A_2)$N— is the covalently bonded form of the corresponding intermediate of formula $(A_1)(A_2)$N—H, wherein said intermediate of formula $(A_1)(A_2)$N—H is a pyrimidine of formula

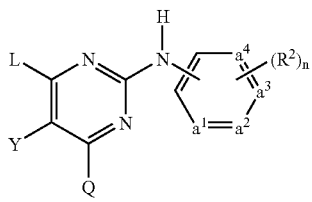

an N-oxide, a pharmaceutically acceptable addition salt, a quaternary amine and a stereochemically isomeric form thereof, wherein -a$^1$=a$^2$-a$^3$=a$^4$- is a bivalent radical of formula —CH=CH—CH=CH—  (a-1);

n is 0, 1, 2, 3, or 5;

each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, aminocarbonyl, nitro, amino, mono- or di(C$_{1-6}$alkyl)amino, polyhalomethyl, polyhalomethyloxy, polyhalomethylthio, —(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

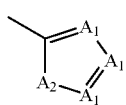

(c)

wherein each A$_1$ independently is N, CH or CR$^6$; and A$_2$ is NH, O, S or NR$^6$;

L is C$_{1-10}$alkyl, C$_{2-10}$alkenyl, C$_{2-10}$alkynyl, C$_{3-7}$cycloalkyl, wherein each of said groups is substituted with one or two substituents independently selected from C$_{3-7}$cycloalkyl, indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy and C$_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined for R$^2$; or L is —X$^1$—R$^3$ or —X$^2$-Alk-R$^{11}$ wherein
  Alk is C$_{1-4}$alkanediyl;
  R$^3$ and R$^{11}$ each independently are phenyl, pyridyl, pyrimidinyl, pyrazinyl or pyridazinyl, wherein each of said aromatic rings may optionally be substituted with one, two, three, four or five substituents each independently selected from the substituents defined in R$^2$; and
  X$^1$ and X$^2$ each independently are —NR$^7$—, —NH—NH—, —N=N—, —O—, —C(=O)—, —CHOH—, —S—, —S(=O)— or —S(=O)$_2$—;

Q is hydrogen, C$_{1-6}$alkyl, halo, polyhaloC$_{1-6}$alkyl or —NR$^4$R$^5$;

R$^4$ and R$^5$ are each independently selected from hydrogen, hydroxy, C$_{1-12}$alkyl, C$_{1-12}$alkyloxy, C$_{1-12}$alkylcarbonyl, C$_{1-12}$alkyloxycarbonyl, C$_{1-12}$alkylthiocarbonyl, aryl, amino, mono- or di(C$_{1-12}$alkyl)amino, mono- or di(C$_{1-2}$alkyl)aminocarbonyl wherein each of the aforementioned C$_{1-2}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-6}$alkyl)amino, polyhalomethyl, polyhalomethyloxy, polyhalomethylthio, —S(=O)$_p$R$^{12}$, —NH—S(=O)$_p$R$^{12}$, —C(=O)R$^{12}$, —NHC(=O)H, —C(=O)NHNH$_2$, —NHC(=O)R$^{12}$, —C(=NH)R$^{12}$, aryl and Het; or R$^4$ and R$^5$ taken together may form pyrrolidinyl, piperidinyl, morpholinyl, azido or mono- or di(C$_{1-12}$alkyl)aminoC$_{1-4}$alkanediyl;

R$^6$ is methyl, amino, mono- or dimethylamino or polyhalomethyl;

R$^7$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy; or C$_{1-6}$alkyloxyC$_{1-6}$alkylcarbonyl substituted with C$_{1-6}$alkyloxycarbonyl;

R$^8$ is C$_{1-6}$alkyl, aryl$^1$ or Het$^1$;

R$^9$ and R$^{10}$ each independently are selected from hydrogen, C$_{1-4}$alkyl, aminoC$_{1-4}$alkyl, or mono- or di(C$_{1-4}$alkyl)aminoC$_{1-4}$alkyl; or R$^9$ and R$^{10}$ are taken together to form a bivalent radical of formula —CH$_2$—CH$_2$-Z-CH$_2$—CH$_2$— with Z being O, NR$^{13}$, CH$_2$, or a direct bond;

R$^{12}$ is methyl, amino, mono- or dimethylamino or polyhalomethyl;

R$^{13}$ is hydrogen, C$_{1-4}$alkyl, aminoC$_{1-4}$alkyl, or mono- or di(C$_{1-4}$alkyl)aminoC$_{1-4}$alkyl;

R$^{14}$ is methyl, amino, mono- or dimethylamino or polyhalomethyl;

Y is hydrogen, hydroxy, halo, C$_{1-6}$alkyl, C$_{3-7}$cycloalkyl, C$_{2-6}$alkenyl optionally substituted with one or more halogen atoms, C$_{2-6}$alkynyl optionally substituted with one or more halogen atoms, C$_{1-6}$alkyl substituted with cyano or —C(=O)R$^{14}$, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^{14}$, —NH—S(=O)$_p$R$^{14}$, —C(=O)R$^{14}$, —NHC(=O)H, —C(=O)NHNH$_2$, —NHC(=O)R$^{14}$, —C(=NH)R$^{14}$ or aryl;

p is 1 or 2;

aryl$^1$ is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, amino, mono- or di(C$_{1-4}$alkyl)amino, polyhaloC$_{1-6}$alkyl and polyhaloC$_{1-6}$alkyloxy;

aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;

Het$^1$ is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl; said partially saturated heterocyclic radical is selected from imidazolinyl, pyrazolinyl, pyrrolinyl, 4,5-dihydro-oxazolyl, 4,5-dihydro-thiazolyl, dihydrofuranyl, and dihydrothienyl; and said aromatic heterocyclic radical is selected from pyrrolyl, furanyl, thienyl, imidazolyl, oxazolyl, thiazolyl, pyridyl, pyrimidinyl, pyrazinyl and pyridazinyl wherein each of said aromatic heterocyclic radicals may optionally be substituted with $C_{1-4}$alkyl;

Het is a saturated, partially saturated or unsaturated (aromatic) heterocyclic radical; said saturated heterocyclic radical is selected from pyrrolidinyl, piperidinyl, homopiperidinyl, piperazinyl, morpholinyl, tetrahydrofuranyl and tetrahydrothienyl wherein each of said saturated heterocyclic radicals may optionally be substituted with an oxo group; said partially saturated heterocyclic radical is selected from imidazolinyl, pyrazolinyl, pyrrolinyl, 4,5-dihydro-oxazolyl, 4,5-dihydro-thiazolyl, dihydrofuranyl, and dihydrothienyl; and said aromatic heterocyclic radical is selected from pyrrolyl, furanyl, thienyl, pyridyl, pyrimidinyl, pyrazinyl and pyridazinyl wherein each of said aromatic heterocyclic radicals may optionally be substituted with hydroxy.

* * * * *